(12) United States Patent
Liang et al.

(10) Patent No.: US 11,276,208 B2
(45) Date of Patent: Mar. 15, 2022

(54) SYSTEM, METHOD AND COMPUTER-ACCESSIBLE MEDIUM FOR ULTRALOW DOSE COMPUTED TOMOGRAPHY IMAGE RECONSTRUCTION

(71) Applicant: THE RESEARCH FOUNDATION FOR THE STATE UNIVERSITY OF NEW YORK, Albany, NY (US)

(72) Inventors: Jerome Zhengrong Liang, Stony Brook, NY (US); Yongfeng Gao, Ridge, NY (US); Yuxiang Xing, Stony Brook, NY (US); Hongbing Lu, Stony Brook, NY (US)

(73) Assignee: The Research Foundation for the State University of New York, Stony Brook, NY (US)

( * ) Notice: Subject to any disclaimer, the term of this patent is extended or adjusted under 35 U.S.C. 154(b) by 0 days.

(21) Appl. No.: 16/622,162

(22) PCT Filed: Jun. 12, 2018

(86) PCT No.: PCT/US2018/037003
§ 371 (c)(1),
(2) Date: Dec. 12, 2019

(87) PCT Pub. No.: WO2018/231757
PCT Pub. Date: Dec. 20, 2018

(65) Prior Publication Data
US 2020/0126271 A1    Apr. 23, 2020

Related U.S. Application Data

(60) Provisional application No. 62/518,282, filed on Jun. 12, 2017.

(51) Int. Cl.
*G06K 9/00* (2006.01)
*G06T 11/00* (2006.01)
(Continued)

(52) U.S. Cl.
CPC ............ *G06T 11/006* (2013.01); *A61B 6/032* (2013.01); *G06T 7/11* (2017.01);
(Continued)

(58) Field of Classification Search
CPC .................................................. G06T 11/006
See application file for complete search history.

(56) References Cited

U.S. PATENT DOCUMENTS 6,950,493 B2    9/2005  Besson
6,999,549 B2    2/2006  Sabol et al.
(Continued)

OTHER PUBLICATIONS

Kubo et al. ("Low dose chest CT protocols (50mAs) as a routine protocol for comprehensive assessment of intrathoracic abnormality", European Journal of Radiology Open 3 (2016) 86-94, Apr. 2016). (Year: 2016).*

(Continued)

*Primary Examiner* — Oneal R Mistry
(74) *Attorney, Agent, or Firm* — ACKnowledge IP P.C.

(57) ABSTRACT

An exemplary system, method, and computer-accessible medium for generating computed tomography ("CT") image(s) of a subject(s) can be provided which can include receiving low dose CT imaging information for the subject(s), where the low dose CT imaging information can be based on a radiation dose of less than about 50 mAs, receiving a priori CT image data, and generating the CT image(s) based on the low dose CT imaging information and the a priori CT image data. A further CT images(s) can be generated based on the CT image(s) and the a priori CT image data. The a priori CT image data can include a set of Markov Random Field (MRF) coefficients derived from high dose or full dose CT image data.

28 Claims, 13 Drawing Sheets

(51) Int. Cl.
  *G06T 7/11*   (2017.01)
  *A61B 6/03*   (2006.01)
(52) U.S. Cl.
  CPC .............. *G06T 2207/10081* (2013.01); *G06T 2207/30008* (2013.01); *G06T 2207/30061* (2013.01); *G06T 2210/41* (2013.01)

(56) References Cited

U.S. PATENT DOCUMENTS

| | | | |
|---|---|---|---|
| 7,471,765 B2 | 12/2008 | Jaffray et al. | |
| 7,627,079 B2 | 12/2009 | Boone | |
| 7,689,017 B2 | 3/2010 | Karl et al. | |
| 7,826,587 B1 | 11/2010 | Langan et al. | |
| 7,872,235 B2 | 1/2011 | Rousso et al. | |
| 7,911,474 B2 | 3/2011 | Li et al. | |
| 8,160,200 B2 | 4/2012 | Tkaczyk et al. | |
| 8,416,914 B2 | 4/2013 | Thibault et al. | |
| 8,467,497 B2 | 6/2013 | Lu et al. | |
| 8,483,463 B2 | 7/2013 | Chen et al. | |
| 8,507,869 B2 | 8/2013 | Asma et al. | |
| 8,538,776 B2 | 9/2013 | Reiner | |
| 8,577,115 B2 | 11/2013 | Gering et al. | |
| 8,611,626 B2 | 12/2013 | Miao et al. | |
| 8,615,118 B2 | 12/2013 | Yi et al. | |
| 8,712,121 B2 | 4/2014 | Wiegert et al. | |
| 8,812,240 B2 | 8/2014 | Yu et al. | |
| 8,835,858 B2 | 9/2014 | Volokh et al. | |
| 8,862,206 B2 | 10/2014 | Wang et al. | |
| 9,129,044 B2 | 9/2015 | Shih et al. | |
| 9,237,874 B2 | 1/2016 | DeMan et al. | |
| 9,251,606 B2 | 2/2016 | Liang et al. | |
| 9,373,159 B2 | 6/2016 | Amroabadi et al. | |
| 9,558,570 B2 | 1/2017 | Liang et al. | |
| 9,592,022 B2 | 3/2017 | Larson | |
| 9,700,264 B2 | 7/2017 | Taguchi et al. | |
| 10,092,253 B2 | 10/2018 | Sodickson et al. | |
| 10,121,267 B2 | 11/2018 | Lin et al. | |
| 10,463,317 B2 | 11/2019 | Tian et al. | |
| 10,638,993 B2 | 5/2020 | Yun et al. | |
| 10,726,587 B2 | 7/2020 | Zhao et al. | |
| 10,765,890 B2 | 9/2020 | Sun et al. | |
| 10,792,006 B2 | 10/2020 | Zhu et al. | |
| 11,062,489 B2 | 7/2021 | Chen et al. | |
| 2013/0202177 A1* | 8/2013 | Bar-Aviv | G06T 11/008 382/131 |
| 2015/0131883 A1 | 5/2015 | Taguchi et al. | |
| 2015/0196265 A1 | 7/2015 | Suzuki | |
| 2015/0287223 A1* | 10/2015 | Bresler | G06T 11/006 382/131 |
| 2016/0078782 A1* | 3/2016 | Meidenbauer | G16H 20/60 434/127 |
| 2016/0328842 A1 | 11/2016 | Ye et al. | |
| 2017/0100078 A1* | 4/2017 | Han | G01R 33/5608 |
| 2018/0228460 A1* | 8/2018 | Singh | G16H 50/70 |
| 2018/0240219 A1* | 8/2018 | Mentl | G06T 11/008 |

OTHER PUBLICATIONS

Low dose chest CT protocol (50 mAs) as a routine protocol forcomprehensive assessment of intrathoracic abnormality (European Journal of Radiology Open 3 (2016) 86-94) (Year: 2016).*

Notification of transmittal of the International Search Report and the Written Opinion dated Sep. 26, 2018 for International Application No. PCT/US2018/37003.

Zhang, H. et al., "Extracting Information from previous full-dose CT scan for knowledge-based Bayesian reconstruction of currentlow-dose CT Images," IEEE Trans Med Imaging, vol. 35, No. 3, pp. 860-870, Mar. 2016.

Xu et al., "Low-Dose X-Ray CT Reconstruction via Dictionary Learning" IEEE Transaction of Medical Imaging, vol. 31, No. 9, pp. 1682-1697, Sep. 2012.

Wang et al., "Hybrid Pre-Log and Post-Log Image Reconstruction for Computed Tomography" IEEE Transactions on Medical Imaging, vol. 36, No. 12, pp. 2457-2465, Dec. 2017.

Rui et al., "Ultra-low dose CT attenuation correction for PET/CT: Analysis of Sparse view data acquisition and Reconstruction algorithms" Phys Med Biol, vol. 60, No. 19, pp. 7437-7460, Oct. 7, 2015.

Wang et al., "An Experimental Study on the Noise Properties of X-ray CT Sinogram Data in Radon Space," Physics in Medicine and Biology, 2008, 53(12): 3327-3341.

Snyder et al., "Compensation for readout noise in CCD images," Journal of Optical Society of America A, 1995, 12(2): 272-283.

P J Rivière, "Penalized-likelihood sinogram smoothing for low-dose CT," Medical Physics, 2005, 32(6): 1676-1683.

Wang et al., "Iterative image reconstruction for CBCT using edge-preserving prior," Medical physics, 2009, 36(1): 252-260.

Whiting et al.,"Signal statistics of X-ray Computed Tomography," Proc. SPIE Medical Imaging, 2002, 4682: 53-60.

Elbakri et al., "Efficient and accurate likelihood for iterative image reconstruction in x-ray computed tomography," Proc. SPIE Medical Imaging, 2003, 5032: 1839-1850.

Lasio et al., "Statistical reconstruction for x-ray computed tomography using energy-integrating detectors," Physics in Medicine and Biology, 2007, 52(8): 2247.

Little et al., "Sinogram restoration in computed tomography with an edge-preserving penalty," Medical Physics, 2015, 42: 1307-1320.

Nett et al., "Low radiation dose C-arm cone-beam CT based on prior image constrained compressed sensing (PICCS): Including compensation for image vol. mismatch between multiple data acquisitions," Proc. SPIE Medical Imaging, 2009, 7258: 725-803.

Ma et al., "Low-dose CT image restoration using previous normal-dose scan," Medical Physics, 2011, 38: 5713-5731.

Shen et al., "Multi-energy CT acquisition and reconstruction with a stepped tube potential scan," Medical Physics, 2015, 42(1): 282-296.

Ouyang et al., "Noise reduction in low-dose cone beam CT by incorporating prior volumetric image information," Medical Physics, 2012, 39: 2569-2577.

Chen et al., "Prior image constrained compressed sensing (PICCS): A method to accurately reconstruct dynamic CT images from highly under-sampled projection data sets," Medical Physics, 2008, 35: 660-663.

Yavuz et al., "Statistical image reconstruction methods for randoms-precorrected PET scans," Medical Image Analysis, 1998, 2(4): 369-378.

Erdogan et al., "Monotonic algorithms for transmission tomography," The 5th IEEE EMBS International Summer School, Biomedical Imaging, pp. 1-5, 2002.

Erdogan et al., "Monotonic algorithms for transmission tomography," IEEE Transactions on Medical, 1999, 18(9): 801-814.

* cited by examiner

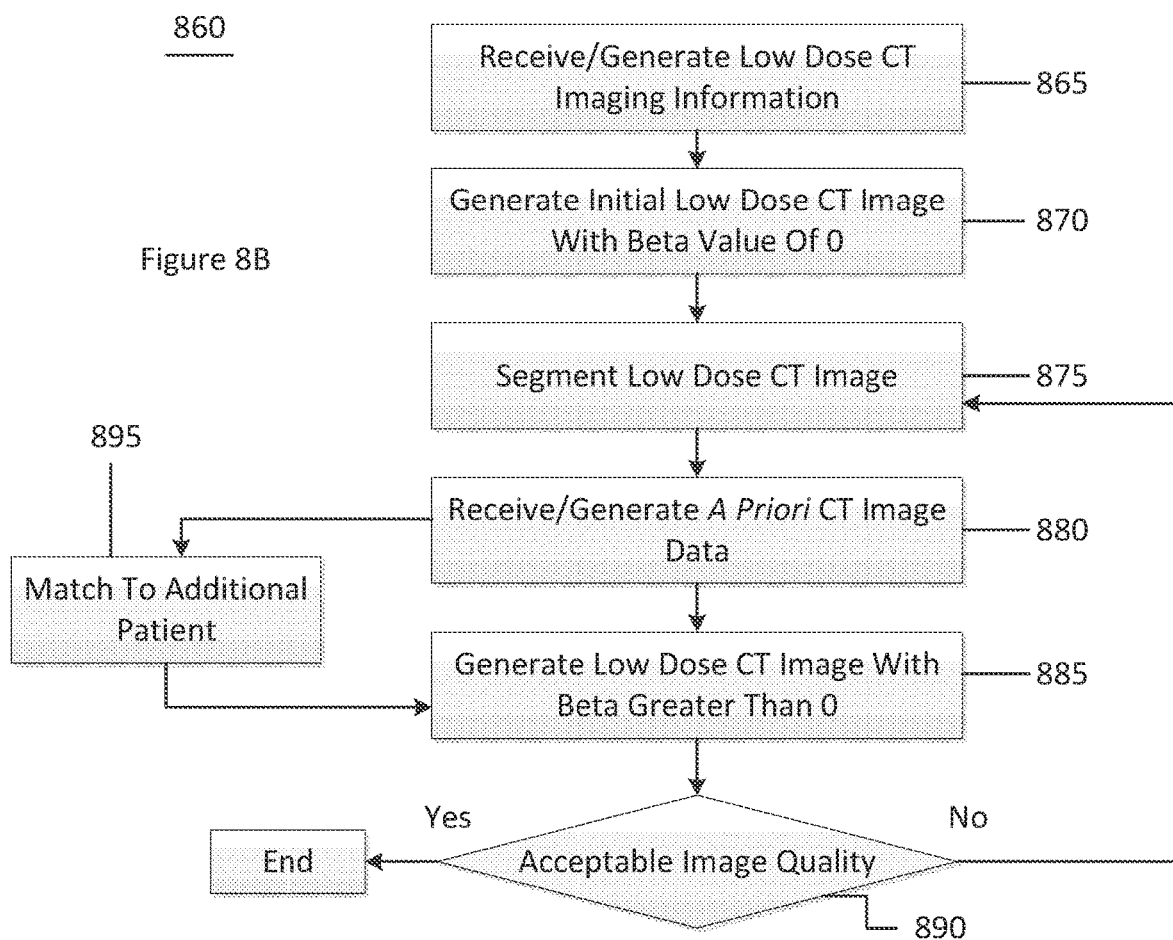

SYSTEM, METHOD AND COMPUTER-ACCESSIBLE MEDIUM FOR ULTRALOW DOSE COMPUTED TOMOGRAPHY IMAGE RECONSTRUCTION

CROSS-REFERENCE TO RELATED APPLICATION(S)

The present application relates to and claims priority from International Patent Application No. PCT/US2018/037003 filed on Jun. 12, 2018 which published as International Publication No. WO 2018/231757 on Dec. 20, 2018 and claims the benefit of U.S. Provisional Patent Application No. 62/518,282, filed on Jun. 12, 2017, the entire disclosures of which are incorporated herein by reference.

STATEMENT REGARDING FEDERALLY SPONSORED RESEARCH

This invention was made with government support under Grant Nos. CA206171 and CA143111, awarded by the National Institutes of Health. The government has certain rights in the invention.

FIELD OF THE DISCLOSURE

The present disclosure relates generally to radiological imaging, and more specifically, to exemplary embodiments of a system, method and computer-accessible medium for ultralow dose computed tomography ("CT") image reconstruction with pre-log shifted-Poisson model and texture-based Markov Random Field ("MRF") prior.

BACKGROUND INFORMATION

Currently, CT operates at high X-ray exposure, in terms of high X-ray flux, for example, 250 mAs, and/or relative high X-ray energy, for example, 120 kVp, to produce diagnostic images for a patient of average size and/or weight. For use in an emergency room, where detection is the major task, the radiation exposure can be reduced to 100 mAs or lower. For pediatric imaging, and preventive screening of smokers for detection of early lung cancer, the preferred radiation exposure is as low as necessary to achieve a specific clinical task. Clinical studies using low-dose CT ("LDCT") screening, where the radiation exposure can be reduced to around 50 mAs, for lung cancer detection have recently shown a 25% reduction of cancer morbidity.

X-ray CT is a widely-used imaging modality. Prior work has been performed to minimize the radiation-associated risk by both hardware and software innovations. For software, statistical modeling for an accurate cost function and iteratively minimizing the cost function for a smooth convergence toward an optimal reconstruction has shown promising performance in maintaining the image quality as compared to the traditional filtered back-projection ("FBP") reconstruction, while at much lower dose levels. To gain additional benefits from the statistical image modeling ("SIM"), reconstruction methods under the Bayesian theory have been focused on two components: (i) the statistical properties of noise in the acquired data and (ii) an appropriate a priori model for the to-be-reconstructed image.

Compound Poisson statistics for the X-ray counts, and Gaussian distribution for the electronic background noise, are commonly used to model the statistical properties of the data which lead to an intractable likelihood term in the Bayesian framework. (See e.g., References 1-4). In one approach to overcoming the intractable problem, an approximation can be made by replacing the compound Poisson with the Poisson and further replacing the summation of the Poisson and Gaussian distributions as a shift Poisson distribution. (See e.g., References 5 and 6).

Work has been done on the a priori modeling of the to-be-reconstructed image in a concerned application. The a priori image modeling is frequently referred to as regularization or penalty in the SIM reconstruction methods. Generally applicable non-linear priors, such as Huber, have been proposed to preserve edges while de-noising at the same time. (See e.g., References 7 and 8). More recently, efforts have been devoted to incorporating information from the source, such as the images from previous full-dose or diagnostic CT ("FDCT") scan (see e.g., References 9-12), and complete data sets (see e.g., References 13 and 14).

There are still challenges in obtaining quality radiological images while using lower, and therefore, safer levels of radiation. Thus, it may be beneficial to provide an exemplary system, method and computer-accessible medium for ultralow dose computed tomography ("ULDCT") image reconstruction with pre-log shifted-Poisson model and texture-based MRF prior which can overcome at least some of the deficiencies described herein above.

SUMMARY OF EXEMPLARY EMBODIMENTS

An exemplary system, method, and computer-accessible medium for generating computed tomography ("CT") image(s) of a subject(s) can be provided which can include receiving low dose CT (LDCT) imaging information for the subject(s), where the LDCT imaging information can be based on a radiation dose of less than about 50 mAs, receiving a priori CT image data, and generating the CT image(s) based on the LDCT imaging information and the a priori CT image data. A further CT images(s) can be generated based on the CT image(s) and the a priori CT image data. The a priori CT image data can include a set of Markov Random Field ("MRF") coefficients derived from high-dose or full-dose CT (FDCT) image data with radiation dose of greater than 100 mAs.

In one embodiment, the a priori CT image data is represented by a plurality of Markov Random Field ("MRF") coefficients. The radiation dose can be less than about 20 mAs. The radiation dose can be less than about 15 mAs. The CT image(s) or the further CT image(s) can be generated based on a beta value or an incident flux. The incident flux can be based on further CT information generated while a CT scanner was empty. The Beta value can be between 4,000 and 6,000.

In some exemplary embodiments of the present disclosure, a further CT image(s) can be generated based on the low dose CT imaging information. The beta value can be modified prior to generating the further CT image(s). An initial low dose CT image can be generated using the low dose CT imaging information and the incident flux. The CT image can be generated using the initial low dose CT image(s). The low dose CT information can be generated using, for example, a CT scanner. The MRF coefficients can include coefficients related to a number of known tissue types, such as four tissue types, which can include lung, fat, bone, and muscle.

The MRF coefficients can be generated based on the a priori CT information. The MRF coefficients can be generated by segmenting the full dose CT images into four tissue types, where the four tissue types include lung, fat, bone, and muscle. The low dose CT image(s) can be segmented into four tissue types, which can include lung, fat, bone, and muscle. The MRF coefficients can include texture information for a plurality of pixels in a full dose CT image. The CT image(s) can be stored in a storage arrangement using a std::map object computer procedure. The a priori CT image data can be based on a full dose CT image(s) of the subject(s). The a priori CT image data can be based on a further subject(s), and an attribute(s) of the subject(s) can be matched with the attribute(s) of the further subject(s).

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIG. 8B is a flow diagram of a further method for generating a CT image according to an exemplary embodiment of the present disclosure.

Figure 1A:
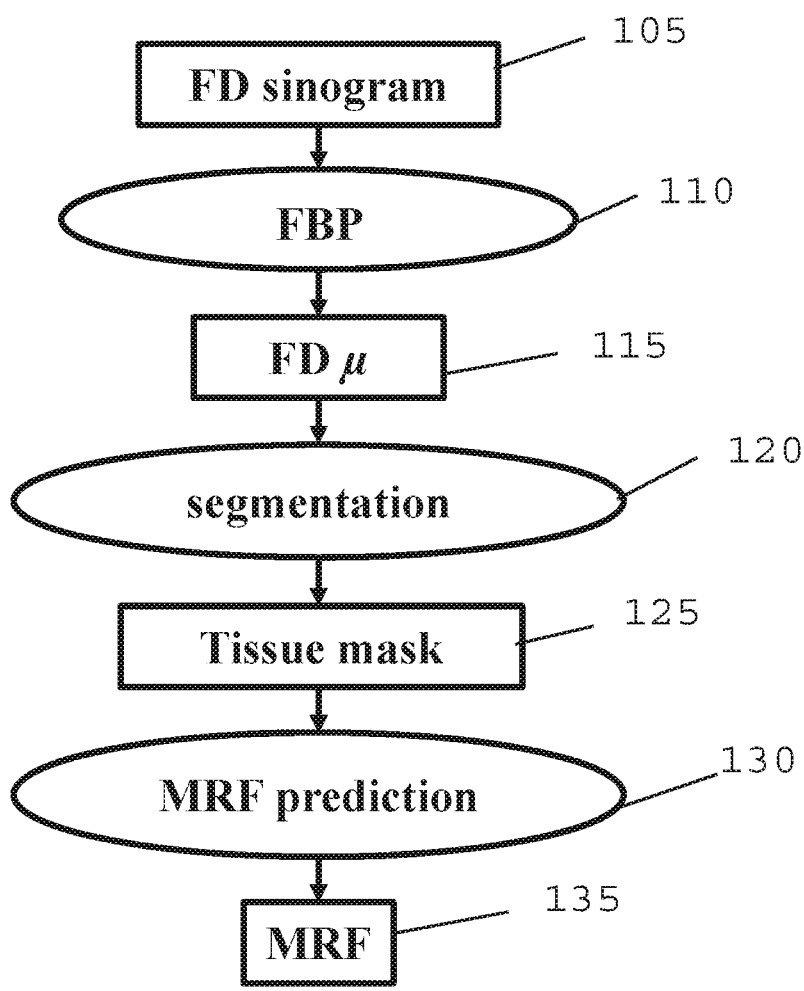
FIG. 1A shows a flow diagram of a method for generating a set of MRF coefficients and generating a CT image according to an exemplary embodiment of the present disclosure.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

The exemplary system, method and computer-accessible medium can provide ULDCT that can achieve the same detection rate of current systems with substantially lower radiation exposure than typical CT systems (e.g., greater than about 50 mAs). For example, the exemplary system, method, and computer-accessible medium, can generate LDCT images using a radiation exposure of about 50 mAs (e.g., about 55 mAs to about 45 mAs). Additionally, the radiation exposure can be less than about 20 mAs (e.g., about 25 mAs to about 15 mAs). Further, images using further reduced radiation exposure levels can also be achieved (e.g., less than about 15 mAs, less than about 10 mAs, or less than about 5 mAs).

As described herein, a high or full dose level can be about 5.0 mSv (e.g., 120 kVp (X-rat tube voltage) and 100 to 300 mAs (X-ray tube current)), a low-dose level can be about 1.5 mSv (e.g. 120 kVp, 30 to 100 mAs), and an ultralow-dose level can be below about 1.0 mSv (e.g. 120 kVP, 20 mAs or less).

The exemplary system, method, and computer-accessible medium, according to an exemplary embodiment of the present disclosure, can accurately model the data acquisition process and all information can be modeled into a theoretically-solid framework. Furthermore, the properties of the majority of normal tissues can be modeled and the acquired data can be shifted to show the properties of a very small portion of abnormal tissues. The data can be acquired in a task-dependent manner to obtain maximum information to achieve the task. The exemplary ULDCT can include (i) more accurate modeling of the data and acquisition process, and then incorporating the data properties more robustly into a theoretically solid framework and (ii) the properties of the normal tissues (e.g. fat, muscle, lung, bone, etc.), which can be a priori known and can be modeled accurately into the theoretically-solid framework. Thus, the acquired data can be processed to show the properties of a very small region where abnormality or pathologically altered issues can occur.

A tractable shifted Poisson model (see e.g., Reference 15) for data statistics can be combined with an exemplary texture-based Markov random field ("MRF") extracted from previous full-dose CT scans (see e.g., Reference 12) to gain full power of SIM reconstruction for ultra-low dose CT imaging.

Acquired data from a polychromatic X-ray CT system can be denoted as a vector $I \in \mathfrak{R}^{M \times 3}$, where M can be the number of data elements. The effective attenuation map of an object can be denoted by a vector $\mu \in \mathfrak{R}^{N \times 1}$, with N being the dimension of lexicographically ordered pixels. With X-ray incident flux (e.g., together with detector efficiency) being $\{I_i^0\}$, where index i can indicate the X-ray toward detector bin i, then the X-ray signals reaching a detector bin i can be expressed as $I_i^0 e^{-[A\mu]_i}$, in an average sense (e.g., $I_i^0$ can be determined accurately by system calibration in the absence of body) according to Beer's law. Matrix A can model the linear system relationship, and can be called a projection matrix of size M×N with its element denoted by $A_{mn}$, and row vector denoted by $A_m$. The acquired data include an additional Gaussian electronic noise, which can assume a mean $m_{e,i}$, and a variance $\sigma_{e,i}^2$, predetermined at each detector bin i.

Exemplary Texture-Preserving Low-Dose Ct Image Reconstruction with Shifted-Poisson Data MRF Texture Model (SP-MRFt)

An artificial random vector can be determined as, for example:

$$I^A \equiv I - m_e + \sigma_e^2. \quad (1)$$

where the mean $m_e$ and variance $\sigma_e^2$ of the background noise can be assumed to be the same for all detector bins for simplicity.

It can be shown that $I^A$ can have its mean and variance both equal to $I_i^0 e^{-[A\mu]_i} + \sigma_e^2$. It has been shown that $[I^A]_+$ can be accurately described by a Poisson distribution. (See e.g., Reference 15). Therefore, a tractable log-likelihood function for $[I^A]_+$ can be obtained as, for example:

$$L(\mu) = \sum_m \{I_m^A \ln(I_m^0 e^{-[A\mu]_m} + \sigma_e^2) - (I_m^0 e^{-[A\mu]_n} + \sigma_e^2)\} \quad (2)$$

It can be beneficial to enforce noise reduction in the case of low dose high noise situations. Texture-based MRF regularization can efficiently incorporate information from previous full-dose images, and can gain effective noise reduction with minimal cost of high-resolution details. (See e.g., Reference 12). Thus, for example:

$$R(\mu) = \frac{1}{2} \sum_{r=1}^{R} \sum_{n \in Rgn(r)} \sum_{n' \in \Omega(n)} w_{nn'}^r (\mu_n - \mu_{n'})^2 \quad (3)$$

where, $\Omega(n)$ can denote neighborhood of pixel n and r indexes a region of certain tissue. Within each region, $w_{nn'}^r$ can be shift-invariant MRF coefficients depending on neighboring relationships. Regions can be segmented and classified based on different texture properties. These MRF coefficients can be determined according to previous full-dose images under the principle of, for example:

$$w_{nn'}^r = \mathrm{argmin} \sum_{n \in Rgn(r)} \sum_{n' \in \Omega(n)} (\mu_n^{FD} - w_{nn'}^r \mu_{n'}^{FD})^2 \forall\, r \quad (4)$$

where, the superscript "FD" can mean full-dose. Eq. (4) can be quadratic, and a close form solution can be obtained as, for example:

$$w^r = \left[ \sum_{n \in Rgn(r)} (\mu_{\Omega_n}^{FD} (\mu_{\Omega_n}^{FD})^T) \right]^{-1} \left[ \sum_{n \in Rgn(r)} (\mu_{\Omega_n}^{FD} \mu_n^{FD}) \right] \quad (5)$$

where, $\mu_\Omega^{FD}$ can denote a lexicographically ordered neighboring pixels around pixel n for notation convenience, and $w^r$ a corresponding vector of MRF coefficients for region r.

Combining Eqs. (2) and (3) can provide an overall objective function to minimize in the framework of a Bayesian MAP (e.g., maximum a posterior) image reconstruction. Thus, for example:

$$\mu = \mathrm{argmin}_\mu \Phi(\mu) = \mathrm{argmin}_\mu (-L(\mu) + \beta R(\mu)) \quad (6)$$

$$= \mathrm{argmin}_\mu \left\{ \begin{array}{l} \sum_m \{(I_m^0 e^{-[A\mu]_n} + \sigma_e^2) - I_m^A \ln(I_m^0 e^{-[A\mu]_\infty} + \sigma_e^2)\} + \\ \frac{\beta}{2} \sum_{r=1}^{R} \sum_{n \leq Region(Y)} \sum_{n' \in \Omega(n)} w_{m'}^r (\mu_n - \mu_{n'})^2 \end{array} \right\}$$

where $\beta$ can be a parameter of balancing the data fidelity term of Eq. (2) and the priori term of Eq. (3).

The objective function can be composed of a non-quadratic part and a quadratic part. The situation of low-dose data acquisition can make the condition of the non-quadratic part worse (e.g., very small condition number). Also, it can be a non-separable function of a large number of unknown variables $\mu$. In response, its separable surrogate function can be determined.

As shown in Eq. (2), for each ray path, a function $h_m(l_m)$ can be denoted as, for example, $h_m(l_m) = (I_m^0 e^- + \sigma_e^2) - I_m^A \ln(I_m^0 e^e + \sigma_e^2)$ with its $1^{st}$ derivative being:

$$h_m'(l_m^k) = I_m^0 e^{-l_m^k} \left( \frac{I_m^A}{I_m^0 e^{-l_m^k} + \sigma_e^2} - 1 \right).$$

In the $k^{th}$ iteration, a global surrogate function for the likelihood term in Eq. (6) can be, for example:

$$\phi(\mu; \mu^k) = \sum_m h_m(l_m^k) + \sum_m h_m'(l_m^k)(l - l_m^k) + \frac{1}{2} \sum_m c_m(l_m^k)(l - l_m^k)^2 = \quad (7)$$

$$\sum_m h_m([A\mu^k]_m) + \sum_m h_m'([A\mu^k]_m)([A\mu]_m - [A\mu^k]_m) +$$

$$\frac{1}{2} \sum_m c_m([A\mu^k]_m)([A\mu]_m - [A\mu^k]_m)^2$$

where, $\mu^k$ can denote the current estimation, $c_m$ can be chosen to ensure monotonic decreasing. Thus, for example:

$$c_m(l_m^k) = \begin{cases} \left[\frac{2}{(l_m^k)^2}\left(\begin{array}{c}I_m^0(1-e^{l_m^k}) - l_m^A \log\frac{I_m^0 + \sigma_e^2}{I_m^0 e^{-l_m^k} + \sigma_c^2} \\ l_m^k I_m^0 e^{l_m^k}\left(\frac{I_m^A}{I_m^0 e^{-l_m^k} + \sigma_c^2} - 1\right)\end{array}\right)\right]_+ & l_m^k > 0 \\ \left[I_m^0\left(1 - \frac{I_m^A \sigma_e^2}{(I_m^0 + \sigma)^2}\right)\right]_+ & \text{else} \end{cases}$$

Because the function for each ray can be quadratic, for example, convex, Eq. (7) can be further relaxed to a separable function by using convexity property based on, for example:

$$[A\mu]_m = \sum_n A_{mn}\mu_n = \sum_n \alpha_{mn}\left[\frac{A_{mn}}{\alpha_{mn}}(\mu_n - \mu_n^k) + l_m^k\right].$$

By choosing $$\alpha_{mn} = \frac{A_{mn}}{|A_m|} \cdot |A_m| = \sum_n A_{mn},$$

the following can be obtained:

$$-L(\mu;\mu^k) \le \sum_n\sum_m \frac{A_{mn}}{|A_m|}\left\{\begin{array}{c}h(l_m^k) + h'_m(l_m^k)(|A_m|(\mu_n - \mu_n^k)) \\ + \frac{1}{2}c_i(l_m^k)(|A_m|(\mu_n - \mu_n^k))^2\end{array}\right\} \quad (8)$$

For the regularization term $R(\mu)$, because it can be quadratic, a separable surrogate function can be obtained using the following:

$$(\mu_n - \mu_{n'})^2 \le \frac{1}{2}(2\mu_n - \mu_n^k - \mu_{n'}^k)^2 + \frac{1}{2}(2\mu_{n'} - \mu_n^k - \mu_{n'}^k)^2,$$

such that $$R(\mu) \le \quad (9)$$

$$\frac{1}{4}\sum_{r=1}^R \sum_{n \in Rgn(r)} \sum_{n' \in \Omega(n)} w_{nn'}^r 1\left((2\mu_n - \mu_n^k - \mu_{n'}^k)^2 + (2\mu_{n'} - \mu_n^k - \mu_{n'}^k)^2\right) =$$

$$\frac{1}{2}\sum_{r=1}^R \sum_{n \in Rgn(r)} \sum_{n' \in \Omega(n)} w_{nn'}^r (2\mu_n - \mu_n^k - \mu_{n'}^k)^2$$

Eqs. (8) and (9) together can provide an overall separable surrogate function, which can include, for example:

$$\Phi(\mu;\mu^k) = \sum_n\sum_m \frac{A_{mn}}{|A_m|}\left\{\begin{array}{c}h(l_m^k) + h'_m(l_m^k)(|A_m|(\mu_n - \mu_n^k)) + \\ \frac{1}{2}c_i(l_m^k)(|A_m|(\mu_n - \mu_n^k))^2\end{array}\right\} + \quad (10)$$

$$\frac{\beta}{2}\sum_{r=1}^R \sum_{n \in Rgn(r)} \sum_{n' \in \Omega(n)} w_{nn'}^r (2\mu_n - \mu_n^k - \mu_{n'}^k)^2$$

According Newton's algorithm, a parallelizable update formula for the exemplary ultralow-dose image reconstruction procedure can be obtained as, for example:

$$\mu_n^{k+1} = \mu_n^k - \left\{\frac{\partial^2 \Phi(\mu;\mu^k)}{\partial \mu_n^2}\right\}_{\mu_n^k}^{-1} \frac{\partial \Phi(\mu;\mu^k)}{\partial \mu_n}\bigg|_{\mu_n^k} \quad (11)$$

with $$\frac{\partial \Phi(\mu;\mu^k)}{\partial \mu_n}\bigg|_{\mu_n^k} = \quad (12)$$

$$\sum_m A_{mn}I_m^0 e^{-l_m^k}\left(\frac{I_m^A}{I_m^0 e^{-l_m^k} + \sigma_e^2} - 1\right) + 2\beta \sum_{n' \in \Omega(n)} w_{nn'}^r(\mu_n^k - \mu_{n'}^k)$$

$$\left\{\frac{\partial^2 \Phi(\mu;\mu^k)}{\partial \mu_n^2}\right\}_{\mu_n^k}^{-1} = \sum_m A_{mn}c_m(l_m^k)|A_m| + 4\beta \sum_{n' \in \Omega(n)} w_{nn'}^r \quad (13)$$

The implementation of the above SP-MRFt procedure can include:
  (i) Segmenting µ from the full dose image into 4 classes.
  (ii) Estimating MRF coefficient $w_{nn'}^r$ for each class according to the full dose image. (See e.g., Reference 12).
  (iii) Initializing image by the FBP reconstruction from the ultralow-dose data;
  (iv) While stop criterion is not met:
    Updating $\mu_n$ using Eqs. (11)-(13) with β=0.
    End if stop criterion is satisfied.
  (v) Segmenting the resulted $\hat{\mu}$ in procedure (iv) into four classes of tissues.
  (vi) Assigning $w_{nn'}^r$ to each pixel according to its class.
  (vii) While stop criterion is not met:
    Updating $\mu_n$ using Eqs. (11)-(13) with a certain β;
    End if stop criterion is satisfied.

FIG. 1A shows an exemplary flow diagram of a method 100 for generating a set of MRF coefficients and generating a database of a priori CT image data. For example full dose sinogram imaging information 105 can be received, and a FBP procedure (see e.g., Eq. (2)) can be used at procedure 110 to generate a set of full dose CT images 115. At procedure 120, the full dose CT images 115 can be segmented to generate tissue mask 125. (See e.g., ref. (12)). A fast segmentation procedure can be used to segment the full dose CT images. The segmentation can include segmenting the chest into four regions or categories of normal tissue. The four categories of normal tissue can include, for example, lung, fat, muscle, and bone. A tissue mask 125 can include borders around the four tissue types, respectively, as well as the borders of the chest regions. A MRF prediction procedure 130 can be performed on the tissue mask 125 to generate a set of MRF coefficients 135 (see e.g., Eqs. (4) and (5)). The generated MRF coefficients for the lung region/mask can be saved as a table (e.g., in a database) for future use (e.g., MRF table 135). Similarly the generated MRF coefficients for the fat region/mask can also be saved as a table (e.g., in a database) for future use, as well as for muscle and bone. Thus, four table tables can be generated for future use when reconstructing LDCT or ULDCT images. (See e.g., FIG. 1 below). It will be appreciated that the use of four tissue types is exemplary and more or less different tissue types could be used.

A set of MRF coefficients corresponding to the lung, bone, fat, and muscle can be generated for each patient image in a database. For example, a database of 1,000 images of 1,000 patients can include generated MRF coefficients for each of the 1,000 patients. Thus, such a database can have 4,000 sets of tissue parameters (e.g., 4 sets of parameters for each of bone, lung, muscle, and fat for each of the 1,000 patients).

At MRF prediction procedure 130, beta can be set to zero. Thus, the MRF term R(w) may not have any effect to the ULDCT image reconstruction of Eq. (6). In the subsequent iterative steps, the beta can be set to a non-zero value such that the stored MRF coefficients (w) can be included in the reconstruction by Eq. (6). The FDCT image can be separated into the four tissue regions (e.g., four tissue masks). Pixels from these images can be used to compute the MRF tissue coefficients. The generated coefficients can be arranged into a 7×7 matrix. For each patient chest, there can be four matrices for lung, fat, muscle, and bone, respectively. When the ULDCT image is constructed at a later time using by Eq. (6) at the kth iteration, the tissue mask of the ULDCT image from the (k−1)-th iteration can be used. Thus, Eq. (6) can be applied to each tissue mask of ULDCT image domain where the corresponding MRF coefficients are included in Eq. (6).

In order to compare neighboring pixels, a 3D volume dataset can be used. Each element in the array can be a cubic voxel. In a 2D image slice, each element can be a square area (e.g., a pixel). Each pixel has a value referred to as an image intensity, and the intensity can be used to determine the MRF coefficients. For example, the intensity differences between from neighboring pixels can be fit into a plurality of equations that can be used to determine the coefficients. The number of equations can be based on the matrix being fit into. Thus, for example, a 7×7 matrix can be generated using 49 equations.

The set of MRF coefficients can be different for each of the four tissue categories (of lung, fat, muscle, and bone), and can be based on an autocorrelation between neighboring pixels (in each tissue type). Each set of coefficients can be fit into a matrix of a particular size depending on the number of coefficients. For example, the MRF coefficients for each region can be lit into a 7×7 matrix. The number of parameters can be chosen by empirically testing neighbors covered by a matrix size of 3×3, 5×5, 7×7, 9×9, or 11×11 format. A 7×7 matrix can be sufficient, because smaller than a 7×7 matrix may not have sufficient information to generate the low dose CT images and greater than a 7×7 may not add sufficient new information to generate a superior image, especially when factoring in the increased processing time that can result from a larger matrix.

Figure 1B:
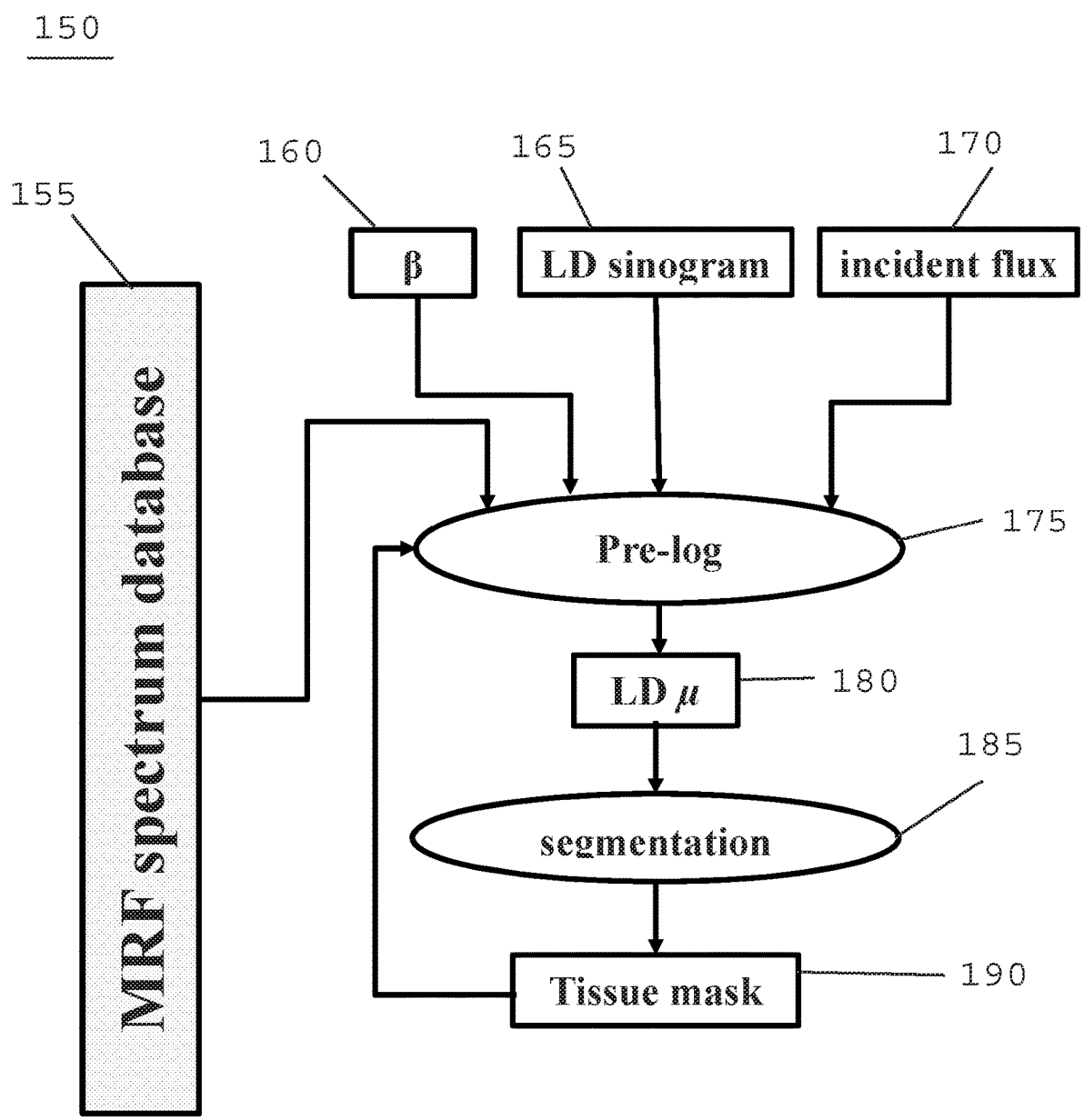
FIG. 1B shows a flow diagram of a method for generating a CT image according to an exemplary embodiment of the present disclosure.

FIG. 1B shows an exemplary flow diagram of a method 150 for generating a LDCT or ULDCT image, which can include an iterative procedure to generate a high quality CT image from low dose sinogram information. Prior to performing an iterative image reconstruction procedure, an initial LDCT or ULDCT image can be generated. The estimate of this initial LDCT or ULDCT image can be performed as follows. For example, the low dose sinogram information 165 and the incident flux 170 can be used to generate the initial set of low dose CT images 180 using a pre-log procedure 175 without using beta or setting beta to zero or a suitable nominal value. (See e.g., Eq. (2), and Eq. (6) without the texture prior R(.) of Eq. (3)). This initial/first run of the pre-log procedure 175 (see e.g., Eq. (6)) can be based only on the low dose sinogram information 165 and the incident flux 170 by the use of Eq. (2) or by setting beta=0 for Eq. (6). From the initial estimated LDCT or ULDCT image 180, a segmentation procedure 185 can be performed to obtain its corresponding four tissue regions of lung, fat, muscle, and bone. These four regions/masks 190 can be saved for use to generate the next iteration of the LDCT or ULDCT image using procedure 175, 180, 185, and 190 as described below.

For example, given four tissue masks 190 of the LDCT or ULDCT image, corresponding tissue MRF coefficients can be obtained (e.g., received) from the MRF spectrum database 155 to construct the second term of Eq. (6). In particular, if a patient has previously had a full dose CT image performed, that previous full dose image will be in a database, and a set of MRF coefficients particular to that patient based on the full dose image can be previously created. Thus, the set of MRF coefficients used to reconstruct the low dose image for a particular patient can be specifically based on that patient's prior full dose image. However, if a patient has not have a prior full dose image generated, the attributes of the patient can be matched to the attributes of another patient that already had a full dose image to use the corresponding MRF coefficients. Attributes can include, but are not limited to, age, sex, height, weight, body mass index, position during scan (e.g., comparing position of low dose image of one patient to the position of the high dose image of a matching patient). Other suitable attributes to more accurately match a patient can be used. Once a match is found in a database, the specific MRF coefficients for the patient with the prior full dose image can be used as the coefficients for the patient without the full dose image.

The first image for a patient can be constructed by the LD sinogram 165 and the incident flux 170. In this iteration, beta can be set to a suitable non-zero value. The data of obtained from procedures 190, 155, 160, 165 and 170 can be input into the pre-log procedure 175 (e.g., of Eq. (6)). From the pre-log operation (e.g., or minimization of Eq. (6)), an updated LDCT or ULDCT image 180 can be generated or obtained. If this updated image is similar to the previously-iterated image, the iterative procedure can end. If the image is not similar, or not sufficiently similar, a further segmentation 185 can be performed on this updated LDCT or ULDCT image for its corresponding tissue masks 190, and the method 150 can be repeated starting at procedure 175 to further update the image. Thus this iterative procedure can repeat until the current iterated result is sufficiently similar to the previously-iterated result. During the iterative procedure, the beta can increase from small (e.g., 1.0) up to 5,000 or 6,000. The beta value 160 can be an empirically determined value, and can be modified (e.g., increased after the initial run) for each iteration of the method 150. Incident flux 170 can be baseline or calibration information obtained using the CT scanner used to generate low dose sinogram information 165 without the patient in the scanner. Thus, incident flux 170 can be used, for example, to eliminate background noise, or any noise or signals introduced by the scanner itself. The incident flux can be determined immediately prior to, or after, the low dose CT scan of the patient. Alternatively, or in addition, the incident flux can be periodically determined irrespective of a scan of the patient.

After the initial set of low dose CT images 180 are generated, these images can be segmented into the four tissue categories (e.g., lung, fat, muscle, and bone), substantially as described above, to generate a tissue mask 190. However, because the procedure 150 is based on the low dose sinogram information 165, the initial set of low dose CT images 180, and the resulting tissue mask can be of a low quality. In order to increase the quality of the generated images a priori data from high dose CT Image data, for example the MRF coefficients 135 generated in method 100, can be used. For example, the MRF coefficients can be stored in a MRF spectrum database. After the initial generation of the low dose images 180 and the resulting tissue mask 190, method 150 can be repeated (e.g., iterated) using the MRF coefficients stored in MRF spectrum database 160 and the low dose sinogram imaging information 165. Additionally, the beta value 160 and/or the incident flux 170 can also be used in the additional iterations. The beta value 160 can be modified from the initial generation of the CT images, and the beta values 160 can also be modified in any subsequent iterations of method 150. For example, the value of beta can increase by 10 in each iteration, although other increments may be used (e.g., by 20, by 50, by 100, by 1,000 etc.). The number of iterations of method 150 can depend on the quality of the generated low dose CT images 180 and the resulting tissue mask 190. Once a sufficient image quality has been achieved, method 150 can end and no additional iterations are needed. The image quality can be determined subjectively by a person evaluating the images or the quality can be automatically determined objectively using a computing arrangement. For example, the density change between images generated at each iteration can be determined. If the density change is below a particular value (e.g., 10%, 5%, 1%, etc.) then the method can end.

The exemplary image reconstruction (e.g., pre-log procedure 175 shown in FIG. 1B) can be expressed as the exemplary pseudocode algorithm, as follows:

---

Begin
  # Initialization:
    Whil (for each pixel j):
      $\mu_j^{old} = 0$ ;

$$\mu_j^{new} = \left[ \mu_j^{old} - \frac{\sum_i A_{ij} N_i^o e^{-l_i^{old}} \left( \frac{N_i^A}{N_i^o e^{-l_i^{old}} + \sigma_e^2} - 1 \right)}{\sum_i A_{ij} (I_i^{old}) \left( \sum_j A_{ij} \right)} \right]_+$$

iteration number > criteria
  end
  # pixel iterated with prior knowledge
  for each segmentation
    image segmentation
    for pixel j inside body mask
      determine tissue type for pixel j;
      choose corresponding MRF coefficients from database;

$$\mu_j^{new} = \left[ \mu_j^{old} - \frac{\sum_i A_{ij} N_i^o e^{-l_i^{old}} \left( \frac{N_i^A}{N_i^o e^{-l_i^{old}} + \sigma_e^2} - 1 \right) + \beta \left( \sum_{k, k \in \Omega(j)} w_{jk} (\mu_j^{old} - \mu_k^{old}) + \sum_{k, j \in \Omega(k)} w_{kj} (\mu_j^{old} - \mu_k^{old}) \right)}{\sum_i A_{ij} c_i(I_i^{old}) \left( \sum_j A_{ij} \right) + 4\beta} \right]_+$$

end $$c_i(I_i^{old}) = \left[ \left( 1 - \frac{N_i^A \sigma_e^2}{(N_i + \sigma_e^2)^2} \right) N_i \right],$$

end
End

---

In order to speed up the exemplary pre-log image reconstructions, the exemplary system, method, and computer-accessible medium can include various strategies to decrease the image reconstruction time. For example, one strategy can be to save the projection matrix $A_{ij}$ into the memory for all iterations instead of calculating it at each iteration. The projection matrix can have be large, with millions of elements, and would can take up a few hundreds gigabytes ("GB") memory space. Thus, accessing all the elements can be time consuming (e.g., in many hours for one iteration). In the exemplary LDCT reconstruction, many of the elements are zero, and only a small fraction (e.g., less than about 5%) of the elements have non-zero elements. By using a std::map object computer operation, the non-zero elements can occupy only about 5 GB of computer space. ((See e.g., Reference 20). Accessing the reduced number of elements and memory space can save approximately 67% of time at each iteration. Additional decreases in processing time can be achieved by the use of the body mask. Only those image pixels inside the body mask may be updated instead of all pixels in the image space. Thus, 45% pixels (e.g., outside the body mask) may not need to be iterated; this can reduce the computing time by 10 to 10% per iteration. Further, when updating $\mu_j^{new}$ by Eq. (6), $A_{ij}$ can be grouped according to the angular sampling around the body, into a few sub-groups in order to speed up the convergence. This updated process (e.g., referred to as the Gauss-Seidel procedure) can be performed for each angular sample or view. If the iteration number can be reduced to a half, the reconstruction time can be cut a half. Additionally, parallel computing with standard computer operation, Open Multi-Processing (MP), can be used to speed up the computing time per iteration, because the updating on one pixel by Eq. (6) may not affect the updating on another pixel. This can save another 67% of time for each iteration. . . .

Exemplary Results

Figure 2:
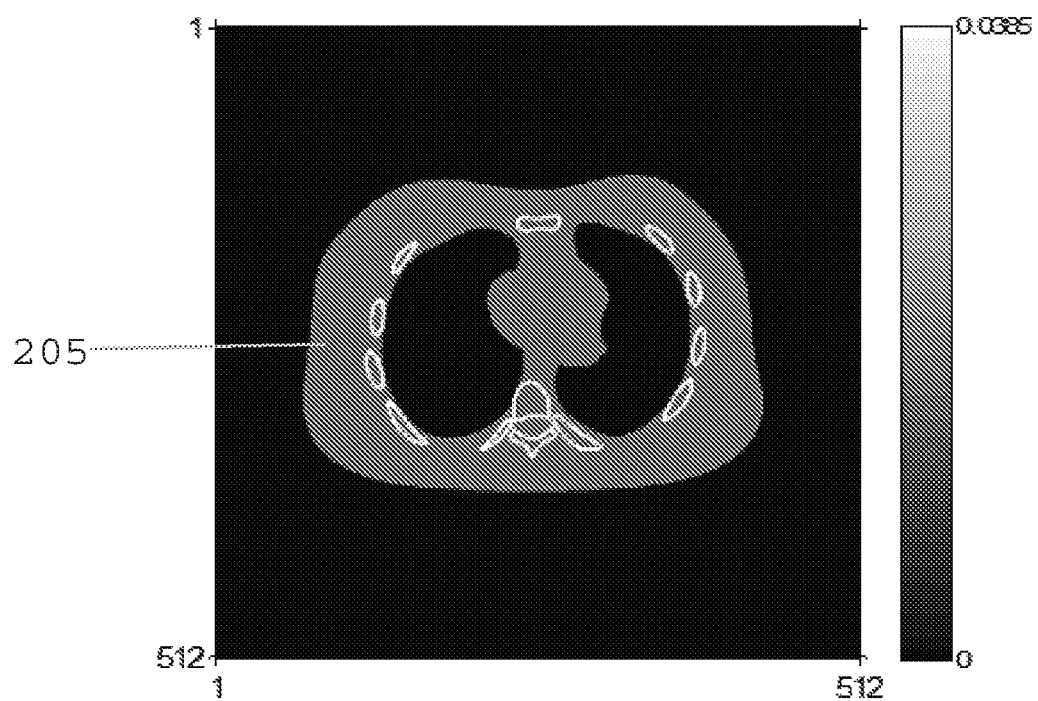
FIG. 2 is an image of a numerical chest phantom according to an exemplary embodiment of the present disclosure.

The exemplary reconstruction procedure was validated on patient ultra-low dose ("ULD") CT data with both numerical simulation and artificial ULD data based on real data. In the numerical simulation, a case with 2000 incident photons and standard deviation=30 for electronic noise was modeled. A 2D image of a chest phantom 205 from NCAT as shown in FIG. 2 was used with materials defined in Table I below.

TABLE I

| matters in numerical chest phantom | |
|---|---|
| tissue | linear attenuation coef. (1/mm) |
| lung | $2.00 * 10^{-5}$ |
| fat | $1.66 * 10^{-2}$ |
| Spine and Rib | $3.85 * 10^{-2}$ |
| spinal | $1.66 * 10^{-2}$ |

Figure 3A:
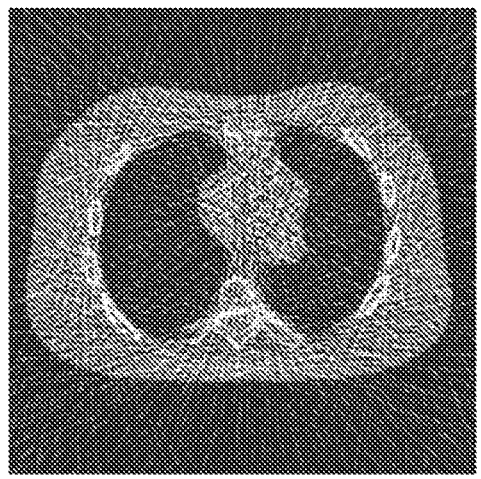
FIG. 3A is a reconstruction image for the cardiac torso chest phantom generated using filtered back-projection according to an exemplary embodiment of the present disclosure.
Figure 3B:
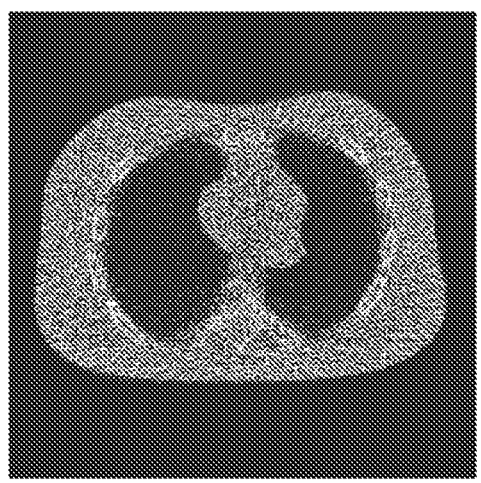
FIG. 3B is a reconstruction image for the cardiac torso chest phantom generated using post-log weighted least squares according to an exemplary embodiment of the present disclosure.
Figure 3C:
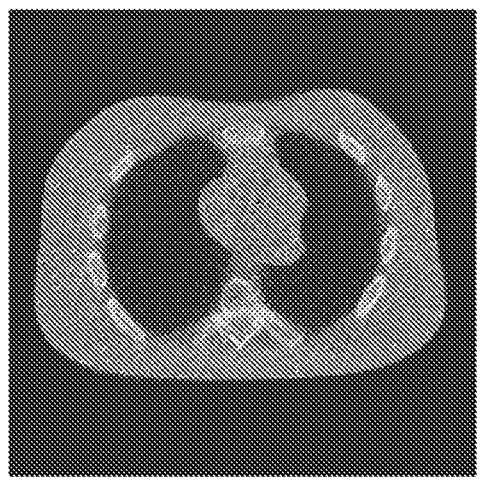
FIG. 3C is a reconstruction image for the cardiac torso chest phantom generated using pre-log shifted Poisson according to an exemplary embodiment of the present disclosure.
Figure 4A:
FIG. 4A is an exemplary reconstruction image generated using full dose filtered back-projection.
Figure 4B:
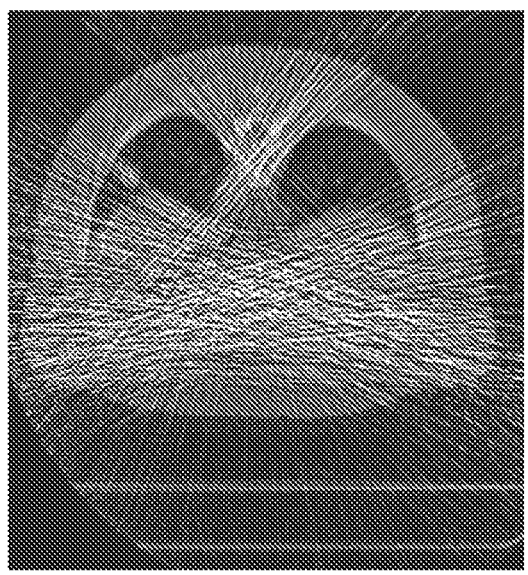
FIG. 4B is a reconstruction image generated using ultralow-dose filtered back-projection according to an exemplary embodiment of the present disclosure.
Figure 4C:
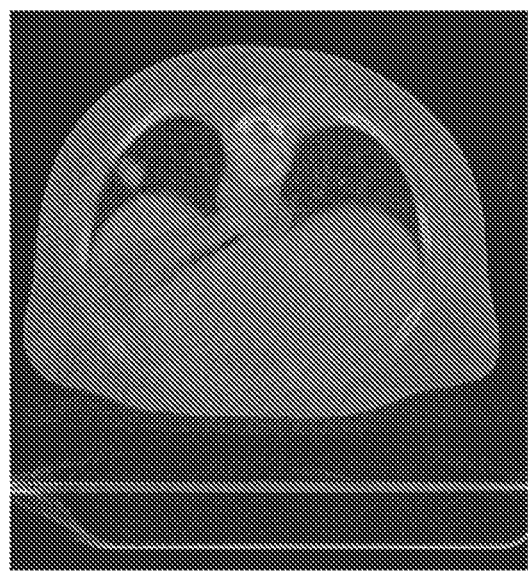
FIG. 4C is a reconstruction image generated using ultralow dose with pre-log shifted Poisson according to an exemplary embodiment of the present disclosure.
Figure 4D:
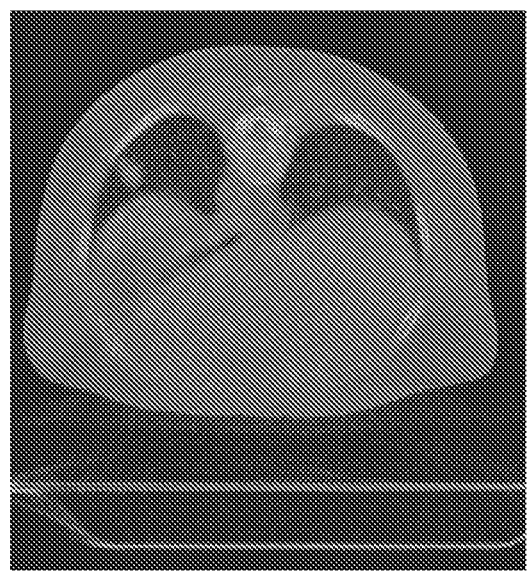
FIG. 4D is a reconstruction image generated using ultralow-dose with pre-log shifted Poisson and texture prior ($\beta$=5000) according to an exemplary embodiment of the present disclosure.

FIGS. 3A-3C illustrate the reconstruction results with FBP (FIG. 3A), post-log weighted least squares ("WLS") (FIG. 3B), and pre-log shifted Poisson model without prior (FIG. 3C). The pre-log shifted Poisson can significantly reduce the streaking artifacts caused by photon starvation in the ULD case. Another ULD CT data was generated based on a real full-dose (e.g., 100 mA) patient data but using 5 mA electrical current level with electronic noise of standard deviation=20 added. Reconstruction results from FBP with full-dose data and ULD data, as well as the pre-log shifted Poisson, and SP-MRFt (Shifted-Poisson Data Model) are compared in FIGS. 4A-4D, which illustrate reconstruction results with different procedures. In particular, FIG. 4A is a reconstruction image generated using full dose filtered back-projection, FIG. 4B is a reconstruction image generated using ultralow-dose filtered back-projection, FIG. 4C is a reconstruction image generated using ultralow dose with pre-log shifted Poisson without the tissue MRF coefficients, and FIG. 4D is a reconstruction image generated using ultralow-dose with pre-log shifted Poisson and the texture MRF coefficients prior (β=5000). The gain for the unknown target of a nodule is due to the known textures of the lung, fat, muscle and bone tissues as an a priori knowledge in our Bayesian image reconstruction.

Figure 5:
FIG. 5 is a reconstruction image generated using ultralow-dose radiation according to an exemplary embodiment of the present disclosure.
Figure 6A:
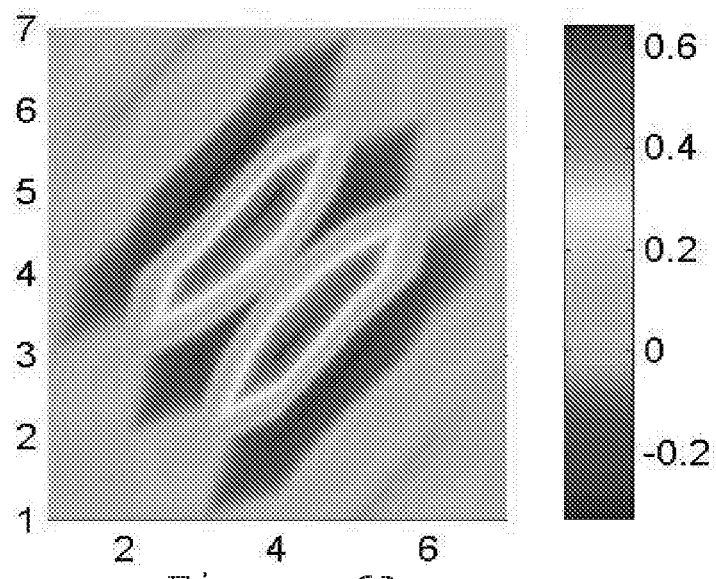
FIG. 6A is a matrix of 7×7 size representing the Markov random field coefficients for lung according to an exemplary embodiment of the present disclosure.
Figure 6B:
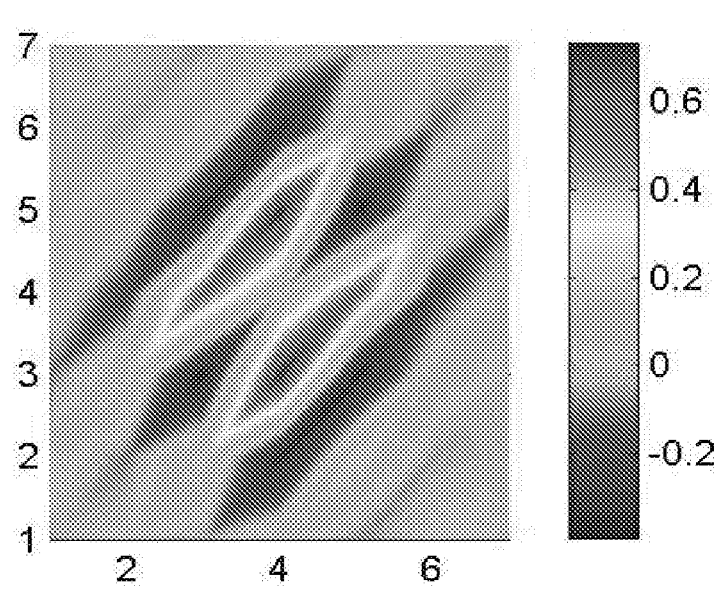
FIG. 6B is a matrix of 7×7 size representing the Markov random field coefficients for bone according to an exemplary embodiment of the present disclosure.
Figure 6C:
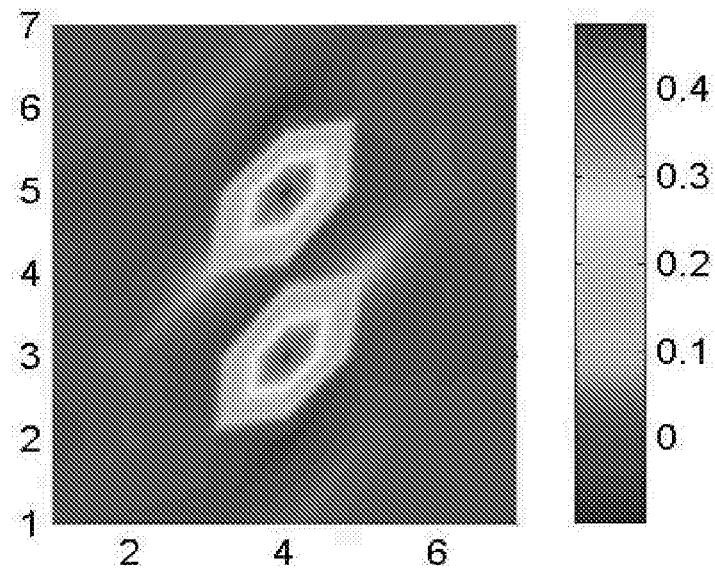
FIG. 6C is a matrix of 7×7 size representing the Markov random field coefficients for muscle according to an exemplary embodiment of the present disclosure.
Figure 6D:
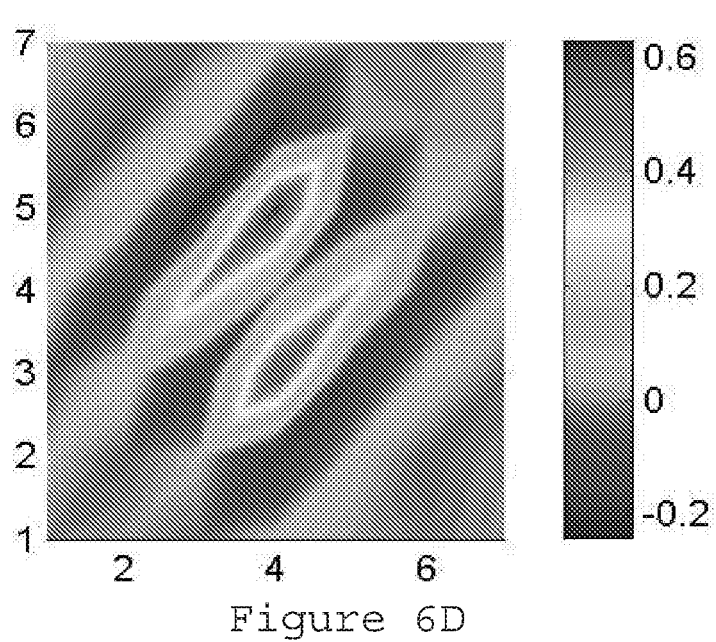
FIG. 6D is a matrix of 7×7 size representing the Markov random field coefficients for fat according to an exemplary embodiment of the present disclosure.

FIG. 5 is a reconstruction image generated using ultralow-dose radiation according to an exemplary embodiment of the present disclosure. The gain for the unknown target of nodule 505 can be due to the known textures of the lung 510, bone 515, fat 520, and muscle 525 tissues as an a priori knowledge in the Bayesian image reconstruction. The results are shown in Table II below.

TABLE 1

Texture distance between the reference full-dose image and the reconstructed ultralow-dose images by the four reconstruction procedures

| ROI | Tissue Type | FBP | GsMRF | Huber | Texture |
|---|---|---|---|---|---|
| 1 | lung | 6.4241 | 5.7532 | 9.9530 | 5.0552 |
| 2 | bone | 8.6492 | 5.6968 | 5.9468 | 2.5173 |
| 3 | fat | 7.3578 | 7.4379 | 7.4194 | 6.6144 |
| 4 | muscle | 11.6797 | 3.8456 | 5.8283 | 2.8951 |
| 5 | lung nodule | 9.9584 | 4.5440 | 5.1329 | 4.3407 |

Tables III and IV below illustrate the results from a lung nodule detection for FBP, spatially-invariant (e.g., Huber), and the exemplary spatially-variant a priori knowledge-based Bayesian image reconstruction (e.g., which can be based on a texture) for primary nodules (Table III) and small nodules (Table IV). The detection gain of nodules is statistically significant, compared to the FBP and Huber methods.

TABLE III primary nodules

Primary nodules only (N = 133)

| Method | missed nodules | Detection rate | Lower bound (95% CI) | Upper bound (95% CI) |
|---|---|---|---|---|
| FBP_100mAs | 0 | 1 | 0.9726 | 1 |
| FBP_40mAs | 1 | 0.9925 | 0.9588 | 0.9998 |
| FBP_20mAs | 4 | 0.9699 | 0.9248 | 0.9917 |
| Huber_40mAs | 0 | 1 | 0.9726 | 1 |
| Huber_20mAs | 3 | 0.9774 | 0.9355 | 0.9953 |
| Texture_40mAs | 0 | 1 | 0.9726 | 1 |
| Texture_20mAs | 2 | 0.985 | 0.9467 | 0.9982 |

TABLE IV small nodules

Small nodules only (N = 66)

| Method | missed nodules | Detection rate | Lower bound (95% CI) | Upper bound (95% CI) |
|---|---|---|---|---|
| FBP_100mAs | 11 | 0.8333 | 0.7213 | 0.9138 |
| FBP_40mAs | 25 | 0.6212 | 0.4934 | 0.7378 |
| FBP_20mAs | 27 | 0.5909 | 0.4629 | 0.7105 |
| Huber_40mAs | 22 | 0.6667 | 0.5399 | 0.778 |
| Huber_20mAs | 22 | 0.6667 | 0.5399 | 0.778 |
| Texture_40mAs | 15 | 0.7727 | 0.653 | 0.8669 |
| Texture_20mAs | 16 | 0.7576 | 0.6364 | 0.8546 |

Tables V and VI below illustrate a statistical analysis of lung nodule detection. A comparison was performed among FBP, spatially-invariant (e.g., Huber), and the exemplary spatially-variant a priori knowledge-based Bayesian image reconstruction (e.g., which can be based on a texture) for primary nodules (Table V) and small nodules (Table VI). The detection gain of nodules is statistically significant when compared to the FBP and Huber methods.

TABLE V

Only primary nodules

| | FBP_100mAs | FBP_40mAs | Huber_40mAs | Texture_40mAs | FBP_20mAs | Huber_20mAs | Texture_20mAs |
|---|---|---|---|---|---|---|---|
| FBP_100mAs | 1 | 1 | 1 | 1 | 0.125 | 0.25 | 0.5 |
| FBP_40mAs | 1 | 1 | 1 | 1 | 0.25 | 0.5 | 1 |
| Huber_40mAs | 1 | 1 | 1 | 1 | 0.125 | 0.25 | 0.5 |
| Texture_40mAs | 1 | 1 | 1 | 1 | 0.125 | 0.25 | 0.5 |
| FBP_20mAs | 0.125 | 0.25 | 0.125 | 0.125 | 1 | 1 | 0.625 |
| Huber_20mAs | 0.25 | 0.5 | 0.25 | 0.25 | 1 | 1 | 1 |
| Texture_20mAs | 0.5 | 1 | 0.5 | 0.5 | 0.625 | 1 | 1 |

TABLE VI

Only small nodules

| | FBP_10mAs | FBP_40mAs | Huber_40mAs | Texture_40mAs | FBP_20mAs | Huber_20mAs | Texture_20mAs |
|---|---|---|---|---|---|---|---|
| FBP_100mAs | 1 | 0.0013 | 0.0433 | 0.5034 | <0.0001 | 0.0192 | 0.3018 |
| FBP_40mAs | 0.0013 | 1 | 0.6476 | 0.0309 | 0.8036 | 0.6476 | 0.0784 |
| Huber_40mAs | 0.0433 | 0.6476 | 1 | 0.0156 | 0.4244 | 1.0000 | 0.3075 |
| Texture_40mAs | 0.5034 | 0.0309 | 0.0156 | 1 | 0.0227 | 0.2100 | 1.0000 |
| FBP_20mAs | <0.0001 | 0.8036 | 0.4244 | 0.0227 | 1 | 0.2668 | 0.0034 |
| Huber_20mAs | 0.0192 | 0.6476 | 1.0000 | 0.2100 | 0.2668 | 1 | 0.0313 |
| Texture_20mAs | 0.3018 | 0.0784 | 0.3075 | 1 | 0.0034 | 0.0313 | 1 |

In the SP-MRFt implementation, MRF coefficients for lung, bone, fat, and muscle are computed from FBP reconstruction of the full-dose data. (See e.g., FIG. 6A-6D). The hyper-parameter β was set to 5000. In the ULD case, FBP reconstruction tends to be of poor image quality. With the pre-log shifted Poisson model, however, most of the structures in the object can be reconstructed to generate clinically useful images, though not of the same image quality as the full-dose FBP. Furthermore, with the texture-based MRF prior, noise in different tissues can be reduced.

Ultralow-dose CT imaging is desired in the field. However, artifacts of ultralow-dose images can be caused by the rays of very weak signals. The exemplary system, method, and computer-accessible medium, according to an exemplary embodiment of the present disclosure, can include an iterative reconstruction procedure based on the pre-log shifted Poisson statistical model together with a texture-based MRF prior constraint for ultralow-dose CT imaging to mitigate this problem. The pre-log shifted Poisson model can characterize the rays with photon starvation problem and provide sufficient reconstructions. Moreover, it can easily combine the texture-based prior to further reduce noise-induced artifacts with little lose in resolution.

Figure 7:
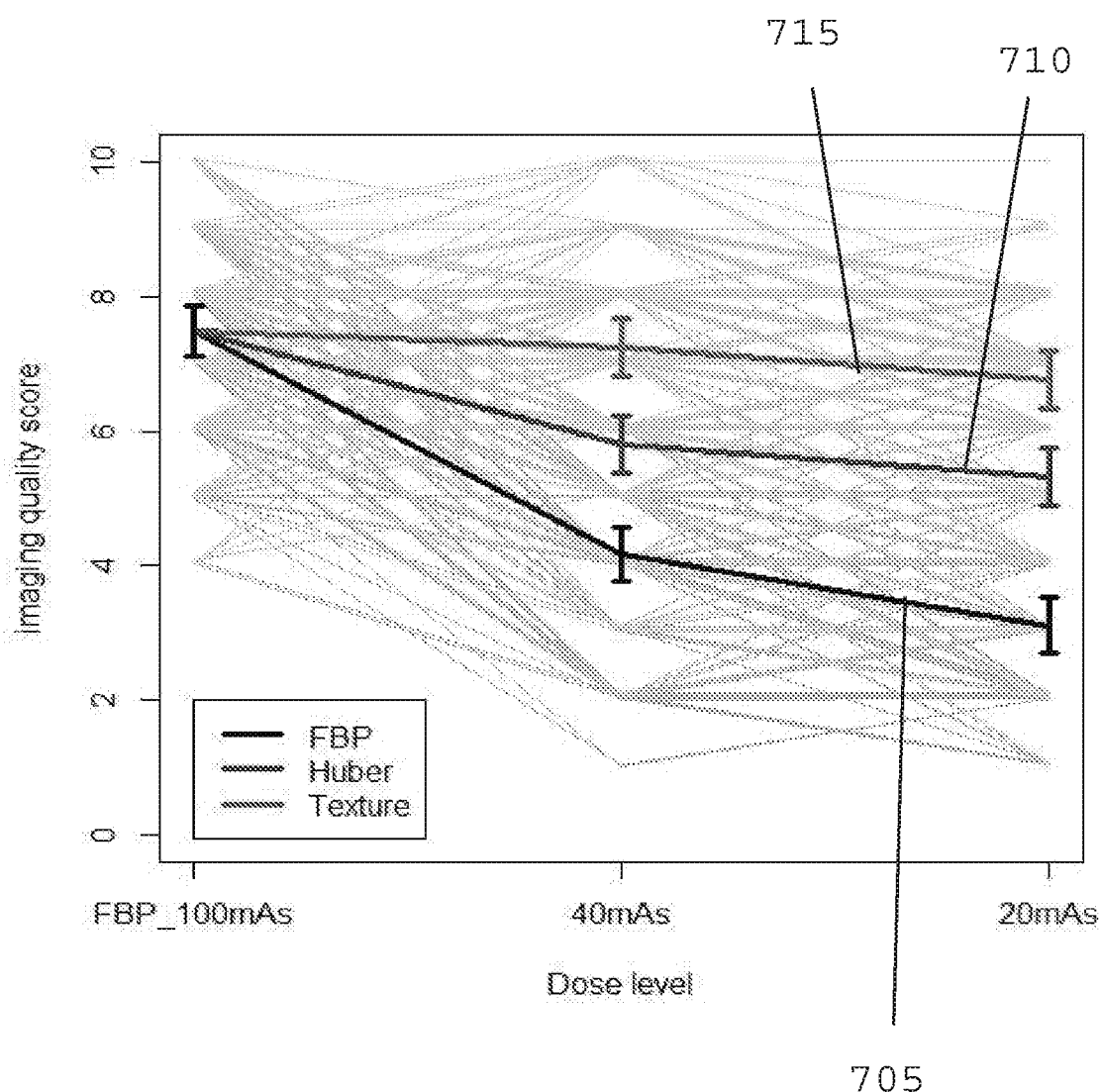
FIG. 7 is a graph illustrating a comparison of the exemplary system, method, and computer-accessible medium to prior reconstruction methods.

FIG. 7 is a graph illustrating a comparison of the exemplary system, method, and computer-accessible medium to prior reconstruction methods. In particular, FIG. 7 compares FBP (line 705), spatially-invariant (e.g., Huber) (line 710), and the exemplary spatially-variant a priori knowledge-based Bayesian image reconstruction, which can be based on a texture (line 715). The diagnostic gain of nodules is statistically significant when compared to the FBP and Huber methods.

Table VII below illustrates a statistical analysis of lung nodule characterization. A comparison was performed for FBP, spatially-invariant (e.g., Huber), and the exemplary spatially-variant a priori knowledge-based Bayesian image reconstruction (e.g., which can be based on a texture). The characterization gain of nodules is statistically significant when compared to the FBP and Huber methods.

TABLE VII

| | Only primary nodules | | | |
|---|---|---|---|---|
| Group | Score drop compared with FBP_100 mAs | Lower Limit of 95% CI | Upper Limit of 95% CI | P-value |
| FBP_20 mAs | 4.39 | 4.09 | 4.69 | <.0001 |
| FBP_40 mAs | 3.33 | 3.03 | 3.63 | <.0001 |
| Huber_20 mAs | 2.17 | 1.87 | 2.47 | <.0001 |
| Huber_40 mAs | 1.71 | 1.41 | 2.00 | <.0001 |
| Texture_20 mAs | 0.73 | 0.43 | 1.02 | <.0001 |
| Texture_40 mAs | 0.26 | −0.04 | 0.55 | 0.0884 |

Figure 8A:
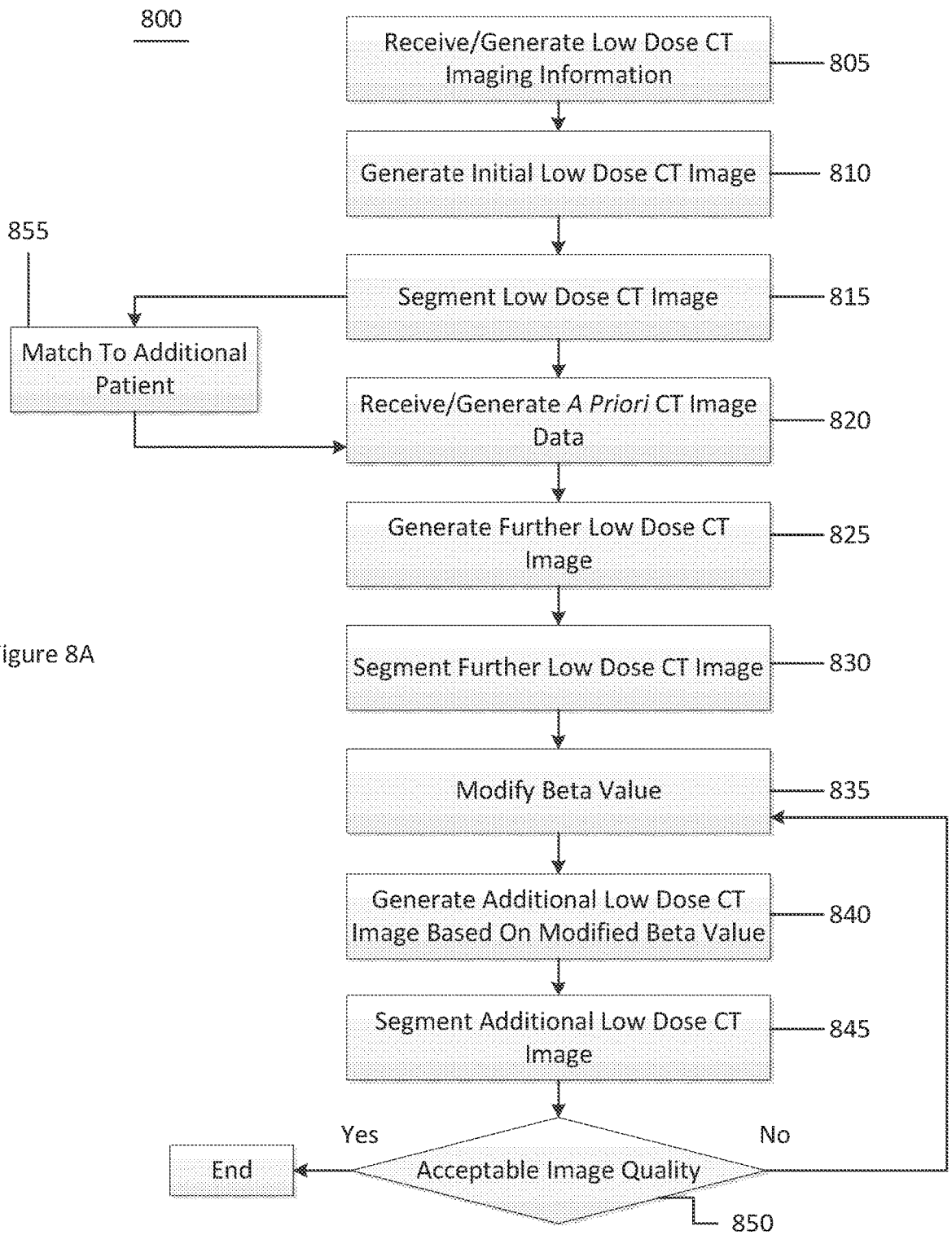
FIG. 8A is a flow diagram of a method for generating a CT image according to an exemplary embodiment of the present disclosure.

FIG. 8A is a flow diagram of a method 800 for generating a CT image according to an exemplary embodiment of the present disclosure. For example, at procedure 805, low dose CT imaging information (e.g., low dose sinogram information) can be generated or received. This information can be used to generate an initial low dose CT image at procedure 810. At procedure 815, the initial low dose CT image can be segmented, such as into, four normal tissue types (e.g., lung, fat, bone, and muscle). If the patient has previously had a full dose CT image performed, then, at procedure 820, a priori CT image data for that specific patient (e.g., MRF coefficients) based on prior full dose CT scan data can be generated or received. If the patient has not had a previous full dose CT image performed, then attributes of the patient can be matched to attributes of a an additional patient that has had a full dose CT image in the database at procedure 855. The a priori CT image data for this patient can be used as a substitute for the patient without the previous full dose CT image.

At procedure 825, a further low dose CT image can be generated using, for example, the a priori MRF coefficients, a beta value, the low dose CT imaging information, an incident flux and the initial low dose CT image. At procedure 830, this further low dose CT image can be segmented into the one of four tissue types. At procedure 835, the beta value can be modified (e.g., increased), and an additional low dose CT image can be generated based on the MRF coefficients, the modified beta value, the low dose CT imaging information, the incident flux and the further low dose CT image. At procedure 845, the additional low dose CT image can be segmented. At procedure 850, a determination can be made as to whether the generated image is of a sufficient quality. If the image is of a sufficient quality, then method 800 can end. If the image is not of a sufficient quality, then method 800 can be iterated starting at procedure 835 by modifying the beta value (e.g., increasing the beta value), and then performing procedures 840 and 850, and performing an image quality check again at procedure 850.

FIG. 8B is a flow diagram of a method 860 for generating a CT image according to an exemplary embodiment of the present disclosure. For example, at procedure 865, low dose CT imaging information (e.g., low dose sinogram information) can be generated or received. This information can be used to generate an initial low dose CT image at procedure 870 with a beta value of zero. At procedure 875, the initial low dose CT image can be segmented, such as into four normal tissue types (e.g., lung, fat, bone, and muscle). If the patient has previously had a full dose CT image performed, then, at procedure 880, a priori CT image data for that specific patient (e.g., MRF coefficients) based on prior full dose CT scan data can be generated or received. If the patient has not had a previous full dose CT image performed, then attributes of the patient can be matched to attributes of a an additional patient that has had a full dose CT image at procedure 895. The a priori CT image data for this patient can be used as a substitute for the patient without the previous full dose CT image At procedure 885, a low dose CT image can be generated using, for example, the a priori MRF coefficients, where the beta value is greater than zero. At procedure 890, a determination can be made as to whether the generated image is of a sufficient quality. If the image is of a sufficient quality, then method 860 can end. If the image is not of a sufficient quality, then method 860 can be iterated starting at procedure 875 by modifying the beta value (e.g., increasing the beta value), and then performing procedures 880 and 885, and performing an image quality check again at procedure 890.

Figure 9:
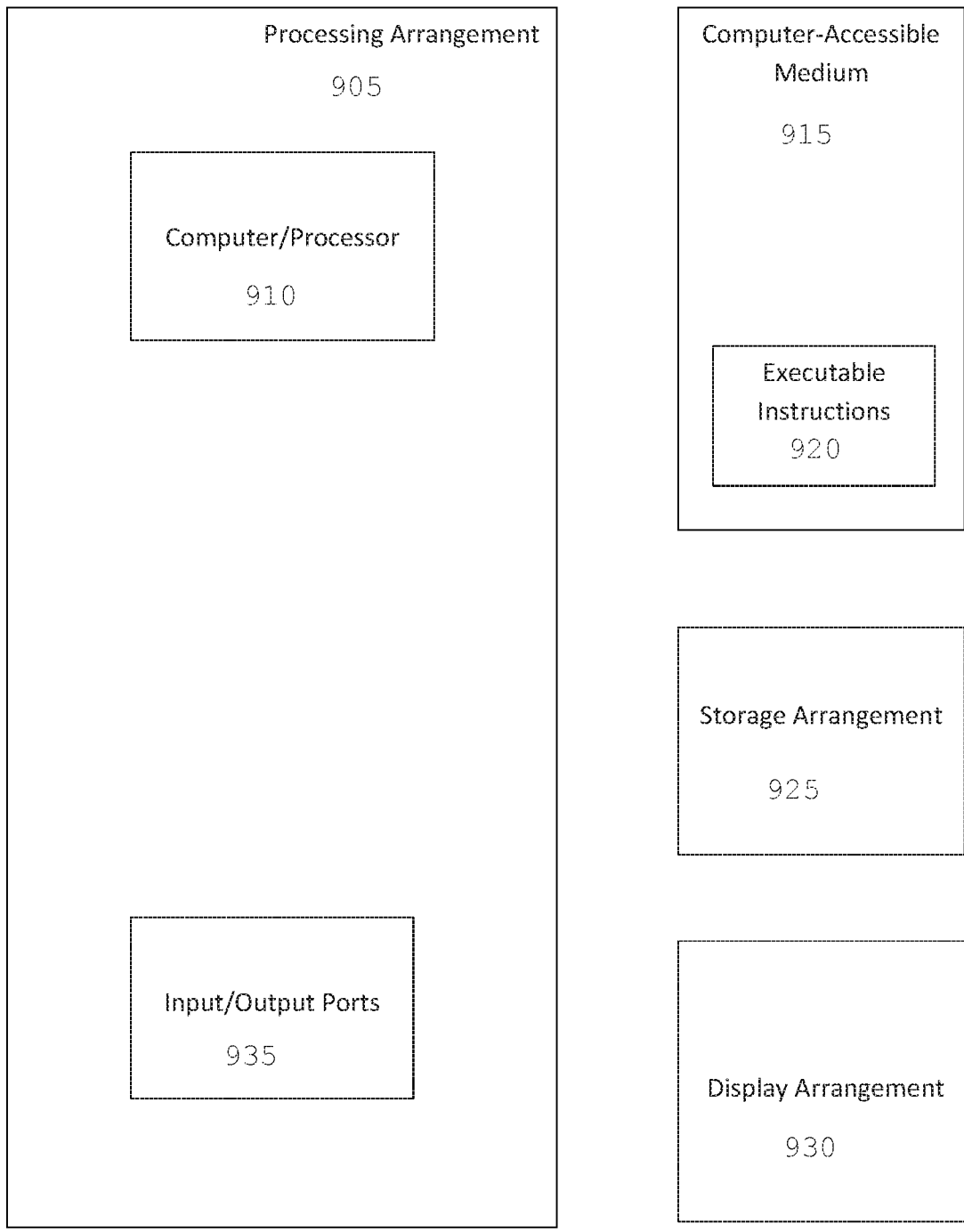
FIG. 9 is a block diagram of an exemplary system in accordance with certain embodiments of the present disclosure.

FIG. 9 shows a block diagram of an exemplary embodiment of a system according to the present disclosure. For example, exemplary procedures in accordance with the present disclosure described herein can be performed by a processing arrangement and/or a computing arrangement (e.g., computer hardware arrangement) 905. Such processing/computing arrangement 905 can be, for example entirely or a part of, or include, but not limited to, a computer/processor 910 that can include, for example one or more microprocessors, and use instructions stored on a computer-accessible medium (e.g., RAM, ROM, hard drive, or other storage device).

As shown in FIG. 9, for example a computer-accessible medium 915 (e.g., as described herein above, a storage device such as a hard disk, floppy disk, memory stick, CD-ROM, RAM, ROM, etc., or a collection thereof) can be provided (e.g., in communication with the processing arrangement 905). The computer-accessible medium 915 can contain executable instructions 920 thereon, which can be used, for example, to generate the information and perform the procedures shown in FIGS. 1A and 1B. In addition or alternatively, a storage arrangement 925 can be provided separately from the computer-accessible medium 915, which can provide the instructions to the processing arrangement 905 so as to configure the processing arrangement to execute certain exemplary procedures, processes, and methods, as described herein above, for example. The storage 925 can also be used to store the CT imaging information and/or the generated CT images, as well as the MRF coefficients.

Further, the exemplary processing arrangement 905 can be provided with or include an input/output ports 935, which can include, for example a wired network, a wireless network, the internet, an intranet, a data collection probe, a sensor, etc. As shown in FIG. 9, the exemplary processing arrangement 905 can be in communication with an exemplary display arrangement 930, which, according to certain exemplary embodiments of the present disclosure, can be a touch-screen configured for inputting information to the processing arrangement in addition to outputting information from the processing arrangement, for example. Further, the exemplary display arrangement 930 and/or a storage arrangement 925 can be used to display and/or store data in a user-accessible format and/or user-readable format.

Exemplary Appendix

Exemplary Mathematical Derivations and Analysis
Pre-Log Data Measurement Model

Let the measurement of X-ray detection in computed tomography (CT) be expressed as, for example:

$$N_i^M \approx \text{Possion}\{\bar{N}_i\} + \text{Gaussian}\{m_e, \sigma_e^2\}, \quad (14)$$

where the measured data $\{N_i^M\}$ can include two parts: (i) the X-ray photon counts, which can follow Poisson statistics with mean $\bar{N}_i$ at detector cell or bin i; and the electronic background noise, which can follow Gaussian statistics with mean $m_e$ and variance $\sigma_e^2$, where the background noise mean and variance can be assumed to be the same for all detector bins. If this assumption is not valid, the mean and variance can have sub-index i as described below.

If the Poisson and Gaussian variables are assumed to be statistically independent from each other, the mean and variance of the measured datum, $N_i^M$, at each detector bin can be derived as, for example:

$$\text{Mean}(N_i^M) = \bar{N}_i + m_e \text{ and } \text{Var}(N_i^M) = \bar{N}_i + \sigma_e^2. \quad (15)$$

A particular quantity or random variable $N_i^A$ can be added, which can produce, for example:

$$N_i^A = N_i^M - m_e + \sigma_e^2, \quad (16)$$

which can be used to prove that the artificial variable can have its variance equals to its mean. Thus, for example:

$$\text{Mean}(N_i^A) = \text{Var}(N_i^A) = \bar{N}_i + \sigma_e^2. \quad (17)$$

An assumption can be made that if a random variable has its variance equals its mean; the random variable can follow Poisson statistics. Thus, for example:

$$[N_i^A]_+ \sim \text{Poisson}(\bar{N}_i + \sigma_e^2), \quad (18)$$

where the condition of $N_i^A = N_i^M - m_e + \sigma_e^2 > 0$ can be satisfied and can be noted by $[N_i^M]_+$ in Eq. (18).

The corresponding log likelihood function can be expressed, assume that all data $\{N_i^A\}$, i=1, 2, 3, . . . , can be statistically independent from each other (where notation $[\ ]_+$ can be ignored for notation simplicity), as, for example:

$$L(N_i^A | \mu) = \quad (19)$$
$$N_i^A \ln(\langle N_i^A \rangle) - \langle N_i^A \rangle = (N_i^M - m_e + \sigma_e^2) \ln(\bar{N}_i + \sigma_e^2) - (\bar{N}_i + \sigma_e^2)$$

$$L(N^A | \mu) = \sum_i \{N_i^A \ln(\langle N_i^A \rangle) - \langle N_i^A \rangle\} = \quad (20)$$
$$\sum_i \{(N_i^M - m_e + \sigma_e^2) \ln(\bar{N}_i + \sigma_e^2) - (\bar{N}_i + \sigma_e^2)\}$$

Exemplary Pre-Log Data Shifted Poisson Model+Texture Prior for Bayesian Ultralow-Dose CT Image Reconstruction
Log-Likelihood with Shifted Poisson Model (with Bear Law)

By the Bear Law of $\bar{N}_i = \bar{N}_i^o e^{-[A\mu]_i}$, where $[A\mu]_i$ can represent the line integral of attenuation coefficients $\mu$ along projection ray i toward detector bin i, notation A can indicate the projection operator, $\bar{N}_i^o$ can be the X-ray flux before reaching the patient body and $\bar{N}_i$ can be defined before as the X-ray flux traversing the body and going toward detector bin i. Thus, for example:

$$L(N^A | \mu) = \sum_i \{N_i^A \ln(\bar{N}_i^o e^{-[A\mu]_i} + \sigma_e^2) - (\bar{N}_i^o e^{-[A\mu]_i} + \sigma_e^2)\}. \quad (21)$$

The maximum likelihood ("ML") solution can be given by, for example:

$$\mu^* = \arg\max_\mu L(N^A | \mu). \quad (22)$$

Exemplary Objective Function with Texture Prior (by Bayesian Theorem)

For simplicity, let $L(\mu) = L(N^A | \mu)$. By Bayesian theorem, the overall objective function can be, for example:

$$\Phi(\mu) = L(\mu) + \beta R(\mu) \quad (23)$$

$$R(\mu) = -\frac{1}{2} \sum_{r=1}^{R} \sum_{j \in \text{Region}(r)} \sum_{k \in \Omega(j)} w_{jk} (\mu_j^r - \mu_k^r)^2, \quad (24)$$

where $\beta$ can be the adjustable parameter of balancing the two terms of data fidelity term, $L(\mu)$, and prior term, $R(\mu)$. The prior term can specify that the body can be composed of regions (with index r) and each region can contain a tissue type. In each tissue type region, a neighborhood $\Omega(.)$ can be selected, which can be a square or cubic window including the pixels or voxels surrounding the central pixel or voxel. The maximum a posterior probability ("MAP") solution can be given by, for example:

$$\mu^* = \arg\max_\mu \Phi(\mu). \quad (25)$$

Exemplary Numerical Optimization Using the Surrogate Function Approach

The following two exemplary expressions can be utilized:

$$L(\mu) = -\sum_i h_i([A\mu]_i) \qquad (26)$$

and $$h_i(l_i) = (\bar{N}_i^\sigma e^{-l_i} + \sigma_e^2) - N_i^A \ln(\bar{N}_i^\sigma e^{-l_i} + \sigma_e^2),$$

where $l_i = [A\mu]_i$ can represent the line integral of the attenuation coefficient along projection ray from X-ray tube/source toward detector bin i, as defined above.

Surrogate Function for Data Fidelity Term $L(\mu)$

For each ray path, the following definitions can be used:

$$q_i(l; l_i^n) = h_i(l_i^n) + h_i'(l_i^n)(l - l_i^n) + \frac{1}{2}c_i(l_i^n)(l - l_i^n)^2, \qquad (27)$$

$$h_i'(l_i^n) = \bar{N}_0 e^{-l_i^N}\left(\frac{N_i^A}{\bar{N}_0 e^{-l_i^N} + \sigma_p^2} - 1\right), \qquad (28)$$

The Global surrogate function for data fidelity term can be, for example:

$$\Phi(\mu; \mu^n) = \sum_i q_i(l; l_i^n) \qquad (29)$$

$$= \sum_i h_i(l_i^n) + \sum_i h_i'(l_i^n)(l - l_i^n) + \frac{1}{2}\sum_i c_i(l_i^n)(l - l_i^n)^2$$

$$= \sum_i h_i([A\mu^n]_i) + \sum_i h_i'([A\mu^n]_i)([A\mu]_i - [A\mu^n]_i) +$$

$$\frac{1}{2}\sum_i c_i([A\mu^n]_i)([A\mu]_i - [A\mu^n]_i)^2$$

The Global surrogate function can be, for example:

$$\Phi(\mu; \mu^n) = \sum_i q_i(l; l_i^n) + \frac{1}{2}\beta\sum_{r=1}^R \sum_{j \in region(r)} \sum_{k \in \Omega(j)} w_{jk}(\mu_j^r - \mu_k^r)^2. \qquad (30)$$

The Separable surrogate for data fidelity term can be, for example:

$$[A\mu]_i = \sum_j A_{ij}\mu_j = \sum_j \{A_{ij}(\mu_j - \mu_j^n) + A_{ij}\mu_j^n\} = \sum_j \{A_{ij}(\mu_j - \mu_j^n)\} + l_i^n \qquad (31)$$

$$= \sum_j \alpha_{ij}\left[\frac{A_{ij}}{\alpha_{ij}}(\mu_j - \mu_j^n)\right] + \sum_j \alpha_{ij}l_i^n = \sum_j \alpha_{ij}\left[\frac{A_{ij}}{\alpha_{ij}}(\mu_j - \mu_j^n) + l_i^n\right],$$

$$\sum_j \alpha_{ij} = 1,$$

where $$q_i(l; l_i^n) \leq \sum_j \alpha_{ij} q_i\left(\frac{A_{ij}}{\alpha_{ij}}(\mu_j - \mu_j^n) + l_i^n; l_i^n\right),$$

because $q_i(\cdot; l_i^n)$ can be convex.

Selecting a specific $$\alpha_{ij}: \alpha_{ij} = \frac{A_{ij}}{\sum_j A_{ij}},$$

can lead to an additive form which can converge more quickly. Thus, the separable surrogate function can be, for example:

$$Q(\mu; \mu^n) = \sum_j \sum_i \frac{A_{ij}}{\sum_j A_{ij}} q_i\left(\left(\sum_j A_{ij}\right)(\mu_i - \mu_j^n) + l_i^n; l_i^n\right). \qquad (32)$$

Exemplary Separable Surrogate for Prior Term

Utilizing $$\varphi(\mu_j - \mu_k) = \varphi\left\{\frac{1}{2}(2\mu_j - \mu_j^n - \mu_k^n) + \frac{1}{2}(-2\mu_k + \mu_j^n + \mu_k^n)\right\} \leq \qquad (33)$$

$$\frac{1}{2}\varphi(2\mu_j - \mu_j^n - \mu_k^n) + \frac{1}{2}\varphi(-2\mu_k - \mu_j^n - \mu_k^n).$$

the separable surrogate function for prior term can be, for example:

$$\frac{1}{2}\sum_{r=1}^R \sum_{j \in region(r)} \sum_{k \in \Omega(j)} w_{jk}(\varphi(2\mu_j - \mu_j^n - \mu_k^n) + \varphi(2\mu_k - \mu_j^n - \mu_k^n)), \qquad (34)$$

which can be in the form of quadratic penalty: $\varphi(\mu_j - \mu_2) = \frac{1}{2}(\mu_j - \mu_k)^2$.

Exemplary Overall Separable Surrogate Function

Combining the above surrogate functions from both data fidelity and prior terms can provide, for example:

$$\Phi(\mu; \mu^n) = \sum_j \sum_i \frac{A_{ij}}{\sum_j A_{ij}} q_i\left(\left(\sum_j A_{ij}\right)(\mu_j - \mu_j^n) + l_i^n; l_i^n\right) + \qquad (35)$$

$$\frac{1}{2}\beta\sum_{r=1}^R \sum_{j \in region(r)} \sum_{k \in \Omega(j)} \frac{1}{2}w_{jk}((2\mu_j^r - \mu_i^n - \mu_k^n)^2 + (2\mu_k^r - \mu_i^n - \mu_k^n)^2)$$

According Newton's algorithm, the following equations can be used to calculate the MAP solution:

$$\mu_j^{n+3} = \mu_j^n - \left\{\frac{\partial^2 \Phi(\mu; \mu^n)}{\partial \mu_j^2}\right\}^{-1}_{\mu_j^k} \frac{\partial \Phi(\mu; \mu^n)}{\partial \mu_j}\bigg|_{\mu_j^k} \qquad (36)$$

$$\frac{\partial \Phi(\mu; \mu^n)}{\partial \mu_j} = \sum_i \frac{A_{ij}}{\sum_j A_{ij}} \frac{\partial \left(\left(\sum_j A_{ij}\right)(\mu_j - \mu_j^n) + l_i^n; l_i^n\right)}{\partial \mu_j} + \qquad (37)$$

$$\beta\left(\sum_{k,k \in \Omega(j)} w_{jk}(2\mu_j - \mu_j^n - \mu_k^n) + \sum_{k,j \in \Omega(k)} w_{jk}(2\mu_j - \mu_k^n - \mu_j^n)\right)$$

$$\left\{\frac{\partial^2 \Phi(\mu; \mu^n)}{\partial \mu_j^2}\right\}\bigg|_{\mu_j^n} = \sum_i \frac{A_{ij}}{\sum_j A_{ij}} \frac{\partial^2 q_i\left(\left(\sum_j A_{ij}\right)(\mu_j - \mu_j^n) + l_i^n; l_i^n\right)}{\partial \mu_j^2} + 4\beta \qquad (38)$$

The resulting iterative calculation algorithm can be expressed as, for example:

$$\mu_j^{n+1} = \mu_j^n - \left\{\frac{\partial^2 \Phi(\mu;\mu^n)}{\partial \mu_j^2}\right\}\bigg|_{\mu_j^n}^{-1} \frac{\partial \Phi(\mu;\mu^N)}{\partial \mu_j}\bigg|_{\mu_j^n} \quad (39)$$

$$= \mu_j^n - \frac{\frac{\partial \Phi(\mu;\mu^n)}{\partial \mu_j}\big|_{\mu_j^n}}{\frac{\partial^2 \Phi(\mu;\mu^n)}{\partial \mu_j^2}\big|_{\mu_j^n}} = \mu_j^n - \frac{\sum_i A_{ij}\overline{N}_0 e^{-l_i^N}\left(\frac{N_i^A}{N_0 e^{-l_i^N}+\sigma_e^2}-1\right)+}{\sum_i A_{ij} c_i(l_i^n)\left(\sum_j A_{ij}\right)+4\beta}$$

While the following strategy is based on the assumption that the patient has both the previous full-dose CT scans, (from which the tissue-specific MRF weighs are extracted), and the current ultralow-dose scans, in practice many of the full-dose CT scans can be collected as a database and can be used for a current ULDCT image reconstruction if this current patient does not have the previous FDCT scan. This iteration method, includes procedures which are pre-reconstruction operations for setting up the tissue texture properties; a procedure for initializing the ultralow-dose reconstruction by two alternative choices; a procedure for updating the ultralow-dose reconstruction by a ML (e.g., maximum likelihood) procedure, for example, setting the beta being zero in Eq. (6), until the image can be reasonably segmented for assignment of the MRF weights in each tissue region; and then performing the MAP (e.g., the beta value be non-zero in Eq. (6)) reconstruction.

The assumption that the patient has the previous full-dose CT scans may not be satisfied in many cases. In such cases, the exemplary system, method, and computer-accessible medium, can modify certain procedures as follows:

From the current patient's physical information, such as body mass index ("BMI"), sex, age, etc., a similar full-dose CT scan can be searched for (e.g., from a FDCT database) to perform the initial procedures on to extract the MRF weights, followed by the remaining procedures. The "similar full-dose CT scan" can be a single scan from a person or a set of scans from a group people who have similar physical information.

Newton's Algorithm

Newton's algorithm can be used to obtain the zero point of one function by using the zero point of its tangential line at n-th iteration. It can be beneficial to obtain the zero point of the overall surrogate function, which can be, for example:

$$\frac{\partial \Phi(\mu;\mu^n)}{\partial \mu_j} = 0. \quad (40)$$

Tangential to $$\frac{\partial \Phi(\mu;\mu^n)}{\partial \mu_j}$$

at $\mu_j^n$ (e.g., the tangential line), can provide, for example:

$$\frac{\partial \Phi(\mu;\mu^n)}{\partial \mu_j} - \frac{\partial \Phi(\mu;\mu^n)}{\partial \mu_j}\bigg|_{\mu_j^n} = \frac{\partial^2 \Phi(\mu;\mu^n)}{\partial \mu_j^2}\bigg|_{\mu_j^n}(\mu-\mu^n) \quad (41)$$

$\mu_j^n$ can be updated to $\mu_j^{n+1}$ using the $\mu_j$ where the tangential crosses zero (e.g., the zero point of tangential line). Thus, for example:

$$\mu_j^{n+1} = \mu_j^n - \left\{\frac{\partial^2 \Phi(\mu;\mu^n)}{\partial \mu_j^2}\right\}\bigg|_{\mu_j^n}^{-1} \frac{\partial \Phi(\mu;\mu^n)}{\partial \mu_j}\bigg|_{\mu_j^n}. \quad (42)$$

Exemplary Data Fidelity Term $$\frac{\partial \Phi(\mu;\mu^n)}{\partial \mu_j}:$$

$$\frac{\partial \Phi(\mu;\mu^n)}{\partial \mu_j} = \sum_i \frac{A_{ij}}{\sum_j A_{ij}} \frac{\partial q_i\left(\left(\sum_j A_{ij}\right)(\mu_j-\mu_j^n)+l_i^n;l_i^n\right)}{\partial \mu_j} \quad (43)$$

$$\sum_i \frac{A_{ij}}{\sum_j A_{ij}} \frac{\partial}{\partial \mu_j}\left(h_i(l_i^n)+h_i'(l_i^n)\left(\left(\sum_j A_{ij}\right)(\mu_j-\mu_j^n)+l_i^n-l_i^n\right)+\right.$$

$$\left.\frac{1}{2}c_i(l_i^n)\left(\left(\sum_j A_{ij}\right)(\mu_j-\mu_j^n)+l_i^n-l_i^n\right)^2\right) =$$

$$\sum_i \frac{A_{ij}}{\sum_j A_{ij}} \frac{\partial}{\partial \mu_j}\left(h_i(l_i^n)+h_i'(l_i^n)\left(\left(\sum_j A_{ij}\right)(\mu_j-\mu_j^n)\right)+\right.$$

$$\left.\frac{1}{2}c_i(l_i^n)\left(\left(\sum_j A_{ij}\right)(\mu_j-\mu_j^n)\right)^2\right) =$$

$$\sum_i \frac{A_{ij}}{\sum_j A_{ij}}\left(h_i'(l_i^n)\left(\sum_j A_{ij}\right)+c_i(l_i^n)\left(\sum_j A_{ij}\right)^2(\mu_j-\mu_j^n)\right)$$

Therefore, for example:

$$\frac{\partial \Phi(\mu;\mu^n)}{\partial \mu_j}\bigg|_{\mu_j^n} = \sum_i \frac{A_{ij}}{\sum_j A_{ij}}\left(h_i'(l_i^n)\left(\sum_j A_{ij}\right)+\right. \quad (44)$$

$$\left. c_i(l_i^n)\left(\sum_j A_{ij}\right)^2(\mu_j-\mu_j^n)\right)\bigg|_{\mu_j^n}$$

$$= \sum_i \frac{A_{ij}}{\sum_j A_{ij}} h_i'(l_i^n)\left(\sum_j A_{ij}\right)$$

$$= \sum_i A_{ij} h_i'(l_i^N)$$

$$= \sum_i A_{ij}\overline{N}_0 e^{-l_i^N}\left(\frac{N_i^A}{\overline{N}_0 e^{-l_i^N}+\sigma_e^2}-1\right)$$

With a data fidelity term of $$\frac{\partial^2 \Phi(\mu;\mu^n)}{\partial \mu_j^2},$$

The following can be provided:

$$\frac{\partial^2 \Phi(\mu; \mu^n)}{\partial \mu_j^2} = \frac{\partial}{\partial \mu_j} \frac{\partial \Phi(\mu; \mu^n)}{\partial \mu_i}$$

$$= \frac{\partial}{\partial \mu_j}\left(\sum_i \frac{A_{ij}}{\sum_i A_{ij}} h_i'(l_i^n)\left(\sum_j A_{ij}\right) + c_i(l_i^n)\left(\sum_j A_{ij}\right)^2 (\mu_j - \mu_j^n)\right)$$

$$= \sum_i \frac{A_{ij}}{\sum_i A_{ij}} c_i(l_i^n) \left(\sum_j A_{ij}\right)^2$$

$$= \sum_i A_{ij} c_i(l_i^n) \left(\sum_j A_{ij}\right)$$

Using a prior term of $$\frac{\partial \Phi(\mu; \mu^n)}{\partial \mu_j}$$

can produce, for example:

$$\frac{\partial (\mu; \mu^n)}{\partial \mu_j} = \frac{\partial}{\partial \mu_j} \frac{1}{2}\beta \sum_{r=1}^{R}\sum_{j \in region(r)}\sum_{k \in \Omega(j)} \frac{1}{2} w_{jk}((2\mu_j^r - \mu_j^n - \mu_k^n)^2 + (2\mu_k^r - \mu_j^n - \mu_k^n)^2) \quad (46)$$

$$= \frac{1}{4}\beta \frac{\partial}{\partial \mu_j} \sum_{k \in \Omega(j)} \frac{1}{2} w_{jk}((2\mu_j^r - \mu_j^n - \mu_k^n)^2 + (2\mu_k^r - \mu_j^n - \mu_k^n)^2)$$

$$= \frac{1}{4}\beta \frac{\partial}{\partial \mu_j} \sum_{k \in \Omega(j)} w_{jk}(2\mu_j - \mu_j^n - \mu_k^n)^2 + \frac{1}{4}\beta \frac{\partial}{\partial \mu_j} \sum_{k \in \Omega(j)} w_{jk}(2\mu_k - \mu_j^n - \mu_k^n)^2$$

$$= \frac{\beta}{4} \sum_{k,k \in \Omega(j)} \frac{\partial}{\partial \mu_j} w_{jk}(2\mu_j - \mu_j^n - \mu_k^n)^2 + \frac{\beta}{4} \sum_{k,j \in \Omega(k)} \frac{\partial}{\partial \mu_j} w_{kj}(2\mu_j - \mu_j^n - \mu_k^n)^2$$

$$= \beta\left(\sum_{k,k \in \Omega(j)} w_{jk}(2\mu_j - \mu_j^n - \mu_k^n) + \sum_{k,j \in \Omega(k)} w_{kj}(2\mu_j - \mu_j^n - \mu_k^n)\right)$$

Thus, for example:

$$\frac{\partial \Phi(\mu; \mu^n)}{\partial \mu_j}\bigg|_{\mu_j^n} = \beta\left(\sum_{k,k \in \Omega(j)} w_{jk}(2\mu_j - \mu_j^n - \mu_k^n) + \sum_{k,j \in \Omega(k)} w_{kj}(2\mu_j - \mu_k^n - \mu_j^n)\right) \quad (47)$$

$$= \beta\left(\sum_{k,k \in \Omega(j)} w_{jk}(\mu_j^n - \mu_k^n) + \sum_{k,j \in \Omega(k)} w_{kj}(\mu_j^n - \mu_k^n)\right)$$

Which can also include a prior term of $$\frac{\partial^2 \Phi(\mu; \mu^n)}{\partial \mu_j^2},$$

which can produce, for example:

$$\frac{\partial^2 \Phi(\mu; \mu'')}{\partial \mu_j^2} = \frac{\partial}{\partial \mu_j} \frac{\partial \Phi(\mu; \mu'')}{\partial \mu_j^2} \quad (48)$$

$$= \frac{\partial}{\partial \mu_j}\beta\left(\sum_{k,k \in \Omega(j)} w_{jk}(2\mu_j - \mu_j^N - \mu_k^N) + \sum_{k,j \in \Omega(k)} w_{kj}(2\mu_j - \mu_k^n - \mu_j^n)\right)$$

$$= \beta \sum_{k,k \in \Omega(j)} \frac{\partial}{\partial \mu_j} w_{jk}(2\mu_j - \mu_k^n - \mu_j^n) + \beta \sum_{k,j \in \Omega(k)} \frac{\partial}{\partial \mu_j} w_{kj}(2\mu_j - \mu_j^n - \mu_k^n)$$

$$= 2\beta \sum_{k,k \in \Omega(j)} w_{j,k} + 2\beta \sum_{k,j \in \Omega(k)} w_{kj}$$

$$= 4\beta$$

In the exemplary case, the prior term can be tissue-specific MRF model, particularly the tissue texture of each tissue type is incorporated, where $w_{jk}$ can be a shift-variant coefficient. As for the voxel at the boundary, there can be overlap. For the voxels inside the region, $$w_{jk}^r = \mathrm{argmin} \sum_{j \in region(r)} \sum_{k \in \Omega(j)} (\mu_j^{FD} - w_{jk}^r \mu_k^{FD})^2, \quad (49)$$

where the superscript index FD can indicate that the CT image was acquired at full- or normal-dose level, and the solution for the MRF weights are, for example:

$$w_{jk}^r = \left[\sum_{j \in region(r)} (\mu_k^{FD}(\mu_k^{FD})^T)\right]^{-1} \left[\sum_{j \in region(r)} (\mu_k^{FD}\mu_k^{FD})\right]. \quad (50)$$

There can be two choices for the coefficient of $c_i(l_i^n)$. One is fixed and the other is iterated.

For the fixed case, $c_i(l_i^n)$ can yields, for example:

$$q(l,l_i^n) = h(l_i^n) + h'(l_i^n)(l - l_i^n) + \tfrac{1}{2} c_i(l_i^n)(l - l_i^n)^2 > h(l), \forall l \in [0, +\infty) \quad (51)$$

h(l) can be expanded at $l_n$, which can be, for example:

$$h(l) = h(l_i^n) + h'(l_i^n)(l - l_i^n) + \tfrac{1}{2} h''(l_i^n)(l - l_i^n)^2 \quad (52)$$

if only the second order is considered. Thus, the following can be chosen:

$$c_i(l_i^n) = \max_{l \in [0, +\infty)} \{\ddot{h}(l)\} = \quad (53)$$

$$\max_{l \in [0, +\infty)} \{\ddot{h}(0), \ddot{h}(\infty)\} = [\ddot{h}(0)]_+ = \left[\left(1 - \frac{N_i^A \sigma_e^2}{(\overline{N}_i + \sigma_e^2)^2}\right)\overline{N}_i\right]_+$$

While, this kind of choice can be too conservative to make the convergence rate slow, it is simple to make the coefficient constant.

The coefficient can also be updated at each iteration, which may not add to the computation time too much, but can decrease the iteration procedures significantly as follows:

$$c_i = (l_i^n) = \begin{cases} \left[\left(2\frac{h_i(0) - h_i(l_i^n)h_i(l_i^n)(l_i^n)}{(l_i^n)^2}\right)\right]_+, & l_i^n > 0 \\ [\ddot{h}(0)]_+, & l_i^n = 0 \end{cases} \quad (54)$$

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entireties.
[1] B R Whiting, S Kingshighway, and S L Mo, "Signal statistics of X-ray Computed Tomography," Proc. SPIE Medical Imaging, 2002, 4682: 53-60.
[2] I A Elbakri and J A Fessler, "Efficient and accurate likelihood for iterative image reconstruction in x-ray computed tomography," Proc. SPIE Medical Imaging, 2003, 5032: 1839-1850.
[3] G M Lasio, B R Whiting, and J F Williamson. "Statistical reconstruction for x-ray computed tomography using energy-integrating detectors," Physics in Medicine and Biology, 2007, 52(8): 2247.
[4] J Wang, H Lu, Z Liang, D Eremina, G Zhang, S Wang, J Chen, and J Manzione, "An Experimental Study on the Noise Properties of X-ray CT Sinogram Data in Radon Space," Physics in Medicine and Biology, 2008, 53(12): 3327-3341.
[5] D L Snyder, C W Helstrom, and A D Lanterman, "Compensation for readout noise in CCD images," Journal of Optical Society of America A, 1995, 12(2): 272-283.
[6] P J Rivière, "Penalized-likelihood sinogram smoothing for low-dose CT," Medical Physics, 2005, 32(6): 1676-1683.
[7] J Wang, T Li, and L Xing. "Iterative image reconstruction for CBCT using edge-preserving prior," Medical physics, 2009, 36(1): 252-260.
[8] K J Little and P J Rivière, "Sinogram restoration in computed tomography with an edge-preserving penalty," Medical Physics, 2015, 42: 1307-1320.
[9] B Nett, J Tang, B Aagaard-Kienitz, H Rowley, and G Chen, "Low radiation dose C-arm cone-beam CT based on prior image constrained compressed sensing (PICCS): Including compensation for image volume mismatch between multiple data acquisitions," Proc. SPIE Medical Imaging, 2009, 7258: 725-803.
[10] J Ma, J Huang, Q Feng, H Zhang, H Lu, Z Liang, and W Chen, "Low-dose CT image restoration using previous normal-dose scan," Medical Physics, 2011, 38: 5713-5731.
[11] L Ouyang, T Solberg, and J Wang, "Noise reduction in low-dose cone beam CT by incorporating prior volumetric image information," Medical Physics, 2012, 39: 2569-2577.
[12] H Zhang, H Han, Z Liang, Y Hu, Y Liu, W Moore, J Ma, and H Lu, "Extracting information from previous full-dose CT scan for knowledge-based Bayesian reconstruction of current low-dose CT images," IEEE Transactions on Medical Imaging, 2016, 35(3): 860-70.
[13] G Chen, J Tang, and S Leng, "Prior image constrained compressed sensing (PICCS): A method to accurately reconstruct dynamic CT images from highly undersampled projection data sets," Medical Physics, 2008, 35: 660-663.
[14] L Shen and Y Xing. "Multi-energy CT acquisition and reconstruction with a stepped tube potential scan," Medical Physics, 2015, 42(1): 282-296.
[15] M Yavuz and J A Fessler. "Statistical image reconstruction methods for randoms-precorrected PET scans," Medical Image Analysis, 1998, 2(4): 369-378.
[16] H Erdogan and J A Fessler. "Monotonic algorithms for transmission tomography," The 5th IEEE EMBS International Summer School, Biomedical Imaging, 2002.
[17] https:/onlinecourses.sciencc.psu.eduistat414/node/166.
[18] D. L. Snyder, C. W. Helstrom, and A. D. Lanterman, "Compensation for readout noise in CCD images," Journal of Optical Society of America A, 1995, 12(2): 272-283.
[19] Hakan Erdogan and Jeffrey A. Fessler, "Monotonic algorithms for transmission tomography," IEEE Transactions on Medical, 1999, 18(9): 801-814.
[20] http://www.cplusplus.com/reference/map/map/

What is claimed is:
1. A system for generating at least one diagnostic computed tomography (CT) image of at least one subject, comprising:
a computer hardware arrangement configured to:
receive low dose CT imaging information for the at least one subject, wherein the low dose CT imaging information is based on a radiation dose of less than about 50 mAs
receive a priori CT image data based on high dose CT image information;
generate the at least one diagnostic CT image based on the low dose CT imaging information, the a priori CT image data, and a beta value, wherein the beta value is a weighting value associated with the a priori CT image data;
modify the beta value; and
generate at least one further diagnostic CT image based on the low dose CT imaging information and modified beta value.
2. The system of claim 1, wherein the computer hardware arrangement is further configured to generate at least one further CT image based on the at least one CT image and the a priori CT image data.
3. The system of claim 1, wherein the a priori CT image data comprises a set of Markov Random Field (MRF)

coefficients, representing at least one specific tissue type, derived from high dose CT image data.

4. The system of claim 3, wherein the MRF coefficients include coefficients related to four tissue types.

5. The system of claim 4, wherein the four tissue types include lung, fat, bone, and muscle.

6. The system of claim 3, wherein the computer hardware arrangement is further configured to generate the MRF coefficients.

7. The system of claim 6, wherein the computer hardware arrangement is further configured to generate the MRF coefficients by segmenting the high dose CT image data into four tissue types, wherein the four tissue types include lung, fat, bone, and muscle.

8. The system of claim 3, wherein the MRF coefficients include texture information for a plurality of pixels in the high dose CT image.

9. The system of claim 1, wherein the radiation dose is less than about 20 mAs.

10. The system of claim 1, wherein the radiation dose is less than about 15 mAs.

11. The system of claim 1, wherein the computer hardware arrangement is configured to generate at least one of the at least one diagnostic CT image or the at least one further CT image based on an incident flux.

12. The system of claim 11, wherein the incident flux is based on further CT information generated while a CT scanner was empty.

13. The system of claim 12, wherein the computer hardware arrangement is further configured to generate at least one initial low dose diagnostic CT image using the low dose CT imaging information and the incident flux.

14. The system claim 13, wherein the computer hardware arrangement is further configured to generate the at least one diagnostic CT image using the at least one initial low dose CT image.

15. The system of claim 11, wherein the Beta value is between 4,000 and 6,000.

16. The system of claim 1, wherein the computer hardware arrangement is further configured to generate the low dose CT information using a CT scanner.

17. The system of claim 1, wherein the computer hardware arrangement is further configured to segment the at least one CT image into four tissue types.

18. The system of claim 17, wherein the four tissue types include, lung, fat, bone, and muscle.

19. The system of claim 1, wherein the computer hardware arrangement is further configured to store the at least one CT image in a storage arrangement using a std::map object computer procedure.

20. The system of claim 1, wherein the a priori CT image data is based on at least one full dose CT image of the at least one subject.

21. The system of claim 1, wherein the a priori CT image data is based on at least one further subject, wherein the computer arrangement is further configured to match at least one attribute of the at least one subject with the at least one attribute of the at least one further subject.

22. The system of claim 1, wherein the low dose CT information includes CT image data and CT scanning information.

23. The system of claim 22, wherein the CT scanning information is selected from the group including X-ray tube voltage, X-ray tube current, and the time per rotation of the X-ray tube around the subject.

24. A non-transitory computer-accessible medium having stored thereon computer-executable instructions for generating at least one diagnostic computed tomography (CT) image of at least one subject, wherein, when a computer arrangement executes the instructions, the computer arrangement is configured to perform procedures comprising:
receiving low dose CT imaging information for the at least one subject, wherein the low dose CT imaging information is based on a radiation dose of less than about 50 mAs
receiving a priori CT image data based on high dose CT image information;
generating the at least one diagnostic CT image based on the low dose CT imaging information, the a priori CT image data, and a beta value, wherein the beta value is a weighting value associated with the a priori CT image data;
modifying the beta value; and
generating at least one further diagnostic CT image based on the low dose CT imaging information and modified beta value.

25. A method for generating at least one diagnostic computed tomography (CT) image of at least one subject, comprising:
receiving low dose CT imaging information for the at least one subject, wherein the low dose CT imaging information is based on a radiation dose of less than about 50 mAs
receiving a priori CT image data based on high dose CT image information;
using a computer hardware arrangement, generating the at least one diagnostic CT image based on the low dose CT imaging information, the a priori CT image data, and a beta value, wherein the beta value is a weighting value associated with the a priori CT image data;
modifying the beta value; and
generating at least one further diagnostic CT image based on the low dose CT imaging information and modified beta value.

26. The method of claim 25, wherein the low dose CT information includes CT image data and CT scanning information.

27. The method of claim 26, wherein the CT scanning information is selected from the group including X-ray tube voltage, X-ray tube current, and the time per rotation of the X-ray tube around the subject.

28. A system for generating at least one diagnostic computed tomography (CT) image of at least one subject, comprising:
a computer hardware arrangement configured to:
receive low dose CT imaging information for the at least one subject, wherein the low dose CT imaging information is based on a radiation dose of less than about 50 mAs;
receive a priori CT image data based on high dose CT image information;
generate the at least one diagnostic CT image based on the low dose CT imaging information, the a priori CT image data, and at least one of a beta value or an incident flux, wherein the beta value is a weighting value in the range of about 4000 and 6000 and is associated with the a priori CT image data and the incident flux is based on further CT information generated while a CT scanner was empty.

* * * * *